(12) United States Patent
DiSilvestro et al.

(10) Patent No.: US 8,068,648 B2
(45) Date of Patent: Nov. 29, 2011

(54) METHOD AND SYSTEM FOR REGISTERING A BONE OF A PATIENT WITH A COMPUTER ASSISTED ORTHOPAEDIC SURGERY SYSTEM

(75) Inventors: Mark R. DiSilvestro, Columbia City, IN (US); Jason T. Sherman, Warsaw, IN (US); Sherrod A. Woods, Fort Wayne, IN (US)

(73) Assignee: DePuy Products, Inc., Warsaw, IN (US)

( * ) Notice: Subject to any disclaimer, the term of this patent is extended or adjusted under 35 U.S.C. 154(b) by 1141 days.

(21) Appl. No.: 11/614,423

(22) Filed: Dec. 21, 2006

(65) Prior Publication Data

US 2008/0154127 A1 Jun. 26, 2008

(51) Int. Cl.
*G06K 9/00* (2006.01)

(52) U.S. Cl. ...................................... 382/128
(58) Field of Classification Search ........... 382/128–134
See application file for complete search history.

(56) References Cited

U.S. PATENT DOCUMENTS

| | | |
|---|---|---|
| 3,847,157 A | 11/1974 | Caillouette et al. |
| 4,054,881 A | 10/1977 | Raab |
| 4,063,561 A | 12/1977 | McKenna |
| 4,173,228 A | 11/1979 | Van Steenwyk et al. |
| 4,244,362 A | 1/1981 | Anderson |
| 4,328,548 A | 5/1982 | Crow et al. |
| 4,396,885 A | 8/1983 | Constant |
| 4,422,041 A | 12/1983 | Lienau |
| 4,431,005 A | 2/1984 | McCormick |
| 4,622,644 A | 11/1986 | Hansen |
| 4,652,820 A | 3/1987 | Maresca |
| 4,661,773 A | 4/1987 | Kawakita et al. |
| 4,677,380 A | 6/1987 | Popovic et al. |
| 4,700,211 A | 10/1987 | Popovic et al. |
| 4,710,708 A | 12/1987 | Rorden et al. |
| 4,790,809 A | 12/1988 | Kuntz |
| 4,791,934 A | 12/1988 | Brunnett |
| 4,809,713 A | 3/1989 | Grayzel |
| 4,829,250 A | 5/1989 | Rotier |
| 4,849,692 A | 7/1989 | Blood |

(Continued)

FOREIGN PATENT DOCUMENTS

CA 2517250 A1 9/2004

(Continued)

OTHER PUBLICATIONS

Ip et al., "Arbitrary Facial Views Generation from Two Orthogonal Facial Images", *IEEE*, 1995, pp. 1079-1084.

(Continued)

*Primary Examiner* — Phuoc Tran
*Assistant Examiner* — Alex Liew
(74) *Attorney, Agent, or Firm* — Barnes & Thornburg LLP

(57) ABSTRACT

A method and system for registering a bone of a patient with a computer assisted orthopaedic surgery system includes retrieving an image of the bone having indicia of the position of a magnetic source coupled thereto, determining first data indicative of the position of the magnetic source in a bone coordinate system, determining second data indicative of a correlation between a coordinate system of the image and the bone coordinate system based on the first data; and displaying an image of the bone based on the second data.

23 Claims, 19 Drawing Sheets

U.S. PATENT DOCUMENTS

| | | | |
|---|---|---|---|
| 4,905,698 A | 3/1990 | Strohl, Jr. et al. | |
| 4,943,770 A | 7/1990 | Ashley-Rollman et al. | |
| 5,099,845 A | 3/1992 | Besz et al. | |
| 5,113,136 A | 5/1992 | Hayashi et al. | |
| 5,206,589 A | 4/1993 | Kado et al. | |
| 5,211,165 A | 5/1993 | Dumouline et al. | |
| 5,251,635 A | 10/1993 | Dumouline et al. | |
| 5,253,647 A | 10/1993 | Takahashi | |
| 5,255,680 A | 10/1993 | Darrow et al. | |
| 5,257,636 A | 11/1993 | White | |
| 5,265,610 A | 11/1993 | Darrow et al. | |
| 5,273,025 A | 12/1993 | Sakiyama et al. | |
| 5,377,678 A | 1/1995 | Dumoulin et al. | |
| 5,383,454 A | 1/1995 | Bucholz | |
| 5,389,101 A | 2/1995 | Heibrun et al. | |
| 5,425,382 A | 6/1995 | Golden et al. | |
| 5,438,990 A | 8/1995 | Wahlstrand et al. | |
| 5,456,718 A | 10/1995 | Szymaitis | |
| 5,558,091 A | 9/1996 | Acker et al. | |
| 5,622,169 A | 4/1997 | Golden et al. | |
| 5,631,557 A | 5/1997 | Davidson | |
| 5,648,719 A | 7/1997 | Christensen et al. | |
| 5,694,040 A | 12/1997 | Plagens | |
| 5,711,299 A | 1/1998 | Manwaring et al. | |
| 5,713,946 A | 2/1998 | Ben-Haim | |
| 5,729,129 A | 3/1998 | Acker | |
| 5,731,996 A | 3/1998 | Gilbert | |
| 5,752,513 A | 5/1998 | Acker et al. | |
| 5,761,332 A * | 6/1998 | Wischmann et al. | 382/131 |
| 5,762,064 A | 6/1998 | Polvani | |
| 5,775,322 A | 7/1998 | Silverstein et al. | |
| 5,799,099 A | 8/1998 | Wang et al. | |
| 5,833,608 A | 11/1998 | Acker | |
| 5,834,709 A | 11/1998 | Blonder et al. | |
| 5,842,986 A | 12/1998 | Arvin et al. | |
| 5,879,297 A | 3/1999 | Haynor et al. | |
| 5,902,238 A | 5/1999 | Golden et al. | |
| 5,913,820 A | 6/1999 | Bladen et al. | |
| 5,942,895 A | 8/1999 | Popovic et al. | |
| 5,944,022 A | 8/1999 | Nardella et al. | |
| 5,944,023 A | 8/1999 | Johnson et al. | |
| 5,967,980 A | 10/1999 | Ferre et al. | |
| 5,983,126 A | 11/1999 | Wittkampf | |
| 5,987,349 A * | 11/1999 | Schulz | 600/427 |
| 6,015,414 A | 1/2000 | Werp et al. | |
| 6,052,610 A | 4/2000 | Koch | |
| 6,059,718 A | 5/2000 | Taniguchi et al. | |
| 6,064,905 A | 5/2000 | Webster et al. | |
| 6,073,043 A | 6/2000 | Schneider | |
| 6,076,007 A | 6/2000 | England et al. | |
| 6,104,944 A | 8/2000 | Martinelli | |
| 6,122,538 A * | 9/2000 | Sliwa et al. | 600/407 |
| 6,129,668 A | 10/2000 | Haynor et al. | |
| 6,146,390 A | 11/2000 | Heibrun et al. | |
| 6,147,480 A | 11/2000 | Osadchy et al. | |
| 6,148,823 A | 11/2000 | Hastings | |
| 6,157,853 A | 12/2000 | Blume et al. | |
| 6,161,032 A | 12/2000 | Acker | |
| 6,165,181 A | 12/2000 | Heibrun et al. | |
| 6,167,145 A * | 12/2000 | Foley et al. | 382/128 |
| 6,167,292 A | 12/2000 | Badano et al. | |
| 6,173,715 B1 | 1/2001 | Sinanan et al. | |
| 6,177,792 B1 | 1/2001 | Govari et al. | |
| 6,184,679 B1 | 2/2001 | Popovic et al. | |
| 6,185,448 B1 | 2/2001 | Borovsky | |
| 6,198,963 B1 | 3/2001 | Haim et al. | |
| 6,201,387 B1 | 3/2001 | Govari | |
| 6,203,493 B1 | 3/2001 | Ben-Haim | |
| 6,210,362 B1 | 4/2001 | Ponzi | |
| 6,211,666 B1 | 4/2001 | Acker | |
| 6,212,419 B1 | 4/2001 | Blume et al. | |
| 6,216,028 B1 | 4/2001 | Haynor et al. | |
| 6,230,038 B1 | 5/2001 | Von Gutfeld et al. | |
| 6,235,038 B1 | 5/2001 | Hunter et al. | |
| 6,236,875 B1 | 5/2001 | Bucholz et al. | |
| 6,241,671 B1 | 6/2001 | Ritter et al. | |
| 6,246,900 B1 | 6/2001 | Cosman et al. | |
| 6,263,230 B1 | 7/2001 | Haynor et al. | |
| 6,285,902 B1 | 9/2001 | Kienzle, III et al. | |
| 6,292,678 B1 | 9/2001 | Hall et al. | |
| 6,304,768 B1 | 10/2001 | Blume et al. | |
| 6,304,769 B1 | 10/2001 | Arenson et al. | |
| 6,311,082 B1 | 10/2001 | Creighton, IV et al. | |
| 6,314,310 B1 | 11/2001 | Ben-Haim et al. | |
| 6,321,109 B2 | 11/2001 | Ben-Haim et al. | |
| 6,332,089 B1 | 12/2001 | Acker et al. | |
| 6,341,231 B1 | 1/2002 | Ferre et al. | |
| 6,347,240 B1 | 2/2002 | Foley et al. | |
| 6,366,799 B1 | 4/2002 | Acker et al. | |
| 6,370,224 B1 | 4/2002 | Simon et al. | |
| 6,373,240 B1 | 4/2002 | Govari | |
| 6,374,134 B1 | 4/2002 | Bladen et al. | |
| 6,381,485 B1 | 4/2002 | Hunter et al. | |
| 6,385,472 B1 | 5/2002 | Hall et al. | |
| 6,401,723 B1 | 6/2002 | Garibaldi et al. | |
| 6,402,762 B2 | 6/2002 | Hunter et al. | |
| 6,405,072 B1 | 6/2002 | Cosman | |
| 6,418,335 B2 | 7/2002 | Arvin et al. | |
| 6,424,856 B1 | 7/2002 | Vilsmeier et al. | |
| 6,427,079 B1 | 7/2002 | Schneider et al. | |
| 6,427,314 B1 | 8/2002 | Acker | |
| 6,428,551 B1 | 8/2002 | Hall et al. | |
| 6,430,434 B1 * | 8/2002 | Mittelstadt | 600/426 |
| 6,434,415 B1 | 8/2002 | Foley et al. | |
| 6,442,416 B1 | 8/2002 | Schultz | |
| 6,445,943 B1 | 9/2002 | Ferre et al. | |
| 6,459,924 B1 | 10/2002 | Creighton, IV et al. | |
| 6,474,341 B1 | 11/2002 | Hunter et al. | |
| 6,475,223 B1 | 11/2002 | Werp et al. | |
| 6,490,467 B1 | 12/2002 | Bucholz et al. | |
| 6,491,702 B2 | 12/2002 | Heilbrun et al. | |
| 6,493,573 B1 | 12/2002 | Martinelli et al. | |
| 6,496,713 B2 | 12/2002 | Arvin et al. | |
| 6,498,477 B1 | 12/2002 | Govari et al. | |
| 6,499,488 B1 | 12/2002 | Hunter et al. | |
| 6,505,062 B1 | 1/2003 | Ritter et al. | |
| 6,507,751 B2 | 1/2003 | Blume et al. | |
| 6,511,417 B1 | 1/2003 | Taniguchi et al. | |
| 6,516,212 B1 | 2/2003 | Bladen et al. | |
| 6,522,907 B1 | 2/2003 | Bladen et al. | |
| 6,522,909 B1 | 2/2003 | Garibaldo et al. | |
| 6,524,303 B1 | 2/2003 | Garibaldi | |
| 6,529,761 B2 | 3/2003 | Creighton, IV et al. | |
| 6,535,756 B1 | 3/2003 | Simon et al. | |
| 6,537,196 B1 | 3/2003 | Creighton, IV et al. | |
| 6,539,327 B1 | 3/2003 | Dassot et al. | |
| 6,545,462 B2 | 4/2003 | Schott et al. | |
| 6,546,279 B1 | 4/2003 | Bova et al. | |
| 6,553,326 B1 | 4/2003 | Kirsch et al. | |
| 6,574,492 B1 | 6/2003 | Ben-Haim et al. | |
| 6,574,498 B1 | 6/2003 | Gilboa | |
| 6,580,938 B1 | 6/2003 | Acker | |
| 6,584,174 B2 | 6/2003 | Schubert et al. | |
| 6,593,884 B1 | 7/2003 | Gilboa et al. | |
| 6,611,141 B1 | 8/2003 | Schulz et al. | |
| 6,618,612 B1 | 9/2003 | Acker et al. | |
| 6,622,098 B2 | 9/2003 | Updegrove | |
| 6,625,563 B2 | 9/2003 | Kirsch et al. | |
| 6,633,773 B1 | 10/2003 | Reisfeld | |
| 6,640,127 B1 | 10/2003 | Kosaka et al. | |
| 6,662,034 B2 | 12/2003 | Segner et al. | |
| 6,662,036 B2 | 12/2003 | Cosman | |
| 6,687,531 B1 | 2/2004 | Ferre et al. | |
| 6,690,963 B2 | 2/2004 | Ben-Haim et al. | |
| 6,701,174 B1 | 3/2004 | Krause et al. | |
| 6,701,179 B1 | 3/2004 | Martineli et al. | |
| 6,702,804 B1 | 3/2004 | Ritter et al. | |
| 6,725,080 B2 | 4/2004 | Melkent et al. | |
| 6,733,511 B2 | 5/2004 | Hall et al. | |
| 6,738,656 B1 | 5/2004 | Ferre et al. | |
| 6,740,103 B2 | 5/2004 | Hall et al. | |
| 6,755,816 B2 | 6/2004 | Ritter et al. | |
| 6,757,557 B1 | 6/2004 | Bladen et al. | |
| 6,772,002 B2 | 8/2004 | Schmidt et al. | |
| 6,786,219 B2 | 9/2004 | Garibaldi et al. | |
| 6,817,364 B2 | 11/2004 | Garibaldi et al. | |
| 6,834,201 B2 | 12/2004 | Gillies et al. | |

| | | | |
|---|---|---|---|
| 6,892,090 B2 | 5/2005 | Verard et al. | |
| 6,895,267 B2 | 5/2005 | Panescu et al. | |
| 6,902,528 B1 | 6/2005 | Garibaldi et al. | |
| 6,911,026 B1 | 6/2005 | Hall et al. | |
| 6,920,347 B2 | 7/2005 | Simon et al. | |
| 6,925,339 B2 | 8/2005 | Grimm et al. | |
| 6,934,575 B2 | 8/2005 | Ferre et al. | |
| 6,937,906 B2 | 8/2005 | Terry et al. | |
| 6,947,786 B2 | 9/2005 | Simon et al. | |
| 6,968,846 B2 | 11/2005 | Viswanathan | |
| 6,977,504 B2 | 12/2005 | Wright et al. | |
| 6,977,594 B2 | 12/2005 | Hudman et al. | |
| 6,978,166 B2 | 12/2005 | Foley et al. | |
| 7,525,309 B2 | 4/2009 | Sherman et al. | |
| 2001/0011175 A1 | 8/2001 | Hunter et al. | |
| 2001/0039421 A1 | 11/2001 | Heilbrun et al. | |
| 2002/0016542 A1 | 2/2002 | Blume et al. | |
| 2002/0019644 A1 | 2/2002 | Hastings et al. | |
| 2002/0021124 A1 | 2/2002 | Schott et al. | |
| 2002/0030483 A1 | 3/2002 | Gilboa | |
| 2002/0032380 A1 | 3/2002 | Acker et al. | |
| 2002/0087062 A1 | 7/2002 | Schmidt et al. | |
| 2002/0100486 A1 | 8/2002 | Creighton, IV et al. | |
| 2002/0116043 A1 | 8/2002 | Garibaldi et al. | |
| 2002/0183610 A1 | 12/2002 | Foley et al. | |
| 2002/0188194 A1 | 12/2002 | Cosman | |
| 2003/0006759 A1 | 1/2003 | Govari | |
| 2003/0023161 A1 | 1/2003 | Govari et al. | |
| 2003/0040671 A1 | 2/2003 | Somogyi et al. | |
| 2003/0088179 A1 | 5/2003 | Seeley et al. | |
| 2003/0090265 A1 | 5/2003 | Wan et al. | |
| 2003/0153827 A1 | 8/2003 | Ritter et al. | |
| 2003/0179856 A1 | 9/2003 | Mitschke et al. | |
| 2004/0021507 A1 | 2/2004 | Fischer | |
| 2004/0046558 A1 | 3/2004 | Matsumoto | |
| 2004/0073279 A1 | 4/2004 | Malackowski et al. | |
| 2004/0207396 A1 | 10/2004 | Xiao | |
| 2004/0215071 A1* | 10/2004 | Frank et al. | 600/407 |
| 2004/0232913 A1 | 11/2004 | Schott et al. | |
| 2004/0249262 A1 | 12/2004 | Werp et al. | |
| 2004/0260172 A1 | 12/2004 | Ritter et al. | |
| 2005/0010301 A1 | 1/2005 | Disilvestro et al. | |
| 2005/0015003 A1 | 1/2005 | Lachner et al. | |
| 2005/0027492 A1 | 2/2005 | Taylor et al. | |
| 2005/0059879 A1 | 3/2005 | Sutherland et al. | |
| 2005/0070916 A1 | 3/2005 | Hollstien et al. | |
| 2005/0075561 A1 | 4/2005 | Golden | |
| 2005/0075562 A1 | 4/2005 | Szakelyhidi et al. | |
| 2005/0182315 A1 | 8/2005 | Ritter et al. | |
| 2005/0245821 A1* | 11/2005 | Govari et al. | 600/429 |
| 2005/0273130 A1 | 12/2005 | Sell | |
| 2006/0011999 A1 | 1/2006 | Schott et al. | |
| 2007/0161888 A1 | 7/2007 | Sherman et al. | |
| 2007/0163367 A1 | 7/2007 | Sherman et al. | |
| 2007/0167703 A1 | 7/2007 | Sherman et al. | |
| 2007/0167741 A1 | 7/2007 | Sherman et al. | |
| 2007/0270722 A1 | 11/2007 | Loeb et al. | |
| 2008/0012558 A1* | 1/2008 | Rossler et al. | 324/252 |
| 2009/0189603 A1 | 7/2009 | Sherman et al. | |

FOREIGN PATENT DOCUMENTS

| | | |
|---|---|---|
| DE | 4014947 A1 | 11/1991 |
| DE | 10037491 A1 | 2/2002 |
| EP | 0993804 A1 | 4/2000 |
| EP | 1020734 A2 | 7/2000 |
| EP | 1081647 A1 | 3/2001 |
| EP | 1181891 A2 | 2/2002 |
| EP | 1184684 A2 | 3/2002 |
| EP | 0983018 B1 | 11/2002 |
| EP | 1302172 A1 | 4/2003 |
| EP | 1348394 A1 | 10/2003 |
| EP | 1447055 A1 | 8/2004 |
| EP | 1493384 A1 | 1/2005 |
| EP | 1530057 A2 | 5/2005 |
| EP | 1570781 A1 | 9/2005 |
| EP | 993804 A1 | 12/2005 |
| GB | 1283521 | 7/1972 |
| GB | 2102127 A | 1/1983 |
| JP | 20044283606 | 10/2004 |
| WO | WO 93/04628 | 3/1993 |
| WO | 9509562 A1 | 4/1995 |
| WO | WO 96/08999 A1 | 3/1996 |
| WO | WO 96/41119 A1 | 12/1996 |
| WO | WO 97/48438 A2 | 12/1997 |
| WO | WO 97/49445 A1 | 12/1997 |
| WO | WO 98/32387 A1 | 7/1998 |
| WO | 9849938 A1 | 11/1998 |
| WO | WO 98/49938 A1 | 11/1998 |
| WO | WO 98/52466 A1 | 11/1998 |
| WO | 9949783 A1 | 10/1999 |
| WO | WO 99/59106 A1 | 11/1999 |
| WO | WO 00/15286 A1 | 3/2000 |
| WO | WO 00/27281 A1 | 5/2000 |
| WO | WO 00/51514 A1 | 9/2000 |
| WO | WO 00/74372 A1 | 12/2000 |
| WO | WO 01/17600 A1 | 3/2001 |
| WO | WO 01/22368 A1 | 3/2001 |
| WO | 0124697 A1 | 4/2001 |
| WO | 0130257 A1 | 5/2001 |
| WO | 0237935 A2 | 5/2002 |
| WO | 02062249 A1 | 8/2002 |
| WO | WO 02/103618 A1 | 12/2002 |
| WO | WO 03/051514 A1 | 6/2003 |
| WO | 03090022 A2 | 10/2003 |
| WO | 03096870 A2 | 11/2003 |
| WO | 2004095044 A1 | 11/2004 |
| WO | WO 2005/044081 A2 | 5/2005 |
| WO | 2005067563 A2 | 7/2005 |
| WO | 2005087125 | 9/2005 |
| WO | WO2005/084572 | 9/2005 |
| WO | WO 2005/086062 A1 | 9/2005 |
| WO | WO 2005/087125 A2 | 9/2005 |
| WO | WO 2005/119505 A2 | 12/2005 |

OTHER PUBLICATIONS

Nikkhahe-Dehkordi et al., "3D Reconstruction of the Femoral Bone using Two X-ray Images from Orthogonal Views", Article retrieved from http://www.lab3d.odont.ku.dk/Documents/Pubs-96/FemurCAR96/femur.html , Jul. 20, 2005, 5 pgs.

Lötjönen et al., "Reconstruction of 3-D Geometry Using 2-D Profiles and a Geometric Prior Model", *IEEE Transactions on Medical Imaging*, vol. 18, No. 10, Oct. 1999.

S. Delorme, "Three-Dimensional Modelling and Rendering of the Human Skeletal Trunk from 2D Radiographic Images", Abstract retrieved from http://doi.ieeecomputersociety.org/10/1109/IM.1999. 805382 , 1 pg.

Andrés del Valle et al., "3D Talking Head Customization by Adaptating a Generic Model to One Uncalibrated Picture", *IEEE*, 2001, pp. II-325-328.

Messmer et al., "Volumetric Model Determination of the Tibia Based on 2D Radiographs Using a 2D/3D Database", *Computer Aided Surgery*, vol. 6, 2001, pp. 183-194.

Benameur et al., "3D Biplanar Reconstruction of Scoliotic Vertebrae Using Statistical Models", Abstract retrieved from http://doi.ieeecomputersociety.org/10.1109/CVPR.2001.991014 , 2 pgs.

Laporte et al., "A biplanar reconstruction method based on 2D and 3D contours: application to the distal femur", *Computer Methods in Biomechanics and Biomedical Engineering (Abstract Only)*, Feb. 2003, vol. 6, No. 1, 2 pgs.

Yao et al., "Assessing Accuracy Factors in Deformable 2D/3D Medical Image Registration Using a Statistical Pelvis Model", Abstract retrieved from http://doi.ieeecomputersociety.org/10.1109/ICCV. 2003.1238644 , 1 pg.

Livyatan et al., "Gradient-Based 2-D/3-D Rigid Registration of Fluoroscopic X-Ray to CT", *IEEE Transactions on Medical Imaging*; vol. 22, No. 11, Nov. 2003, pp. 1395-1406.

Rajamani, "A Novel Approach to Anatomical Structure Morphing for Intraoperative Visualization", *Medical Image Computing and Computer-Assisted Intervention—MICCAI 2004, 7th Conference, Saint-Malo, France, Sep. 2004 Proceedings, Part II*, LNCS 3217, pp. 478-485.

Wu et al., "A Two-Level Method for Building a Statistical Shape Atlas", *The Robotics Institute, Carnegie Mellon University, Pittsburgh, PA and CAOS: Institute for Computer Assisted Orthopaedic Surgery, The Western Pennsylvania Hospital, Pittsburgh, PA, 2005, Jun. 2005, 2 pgs.

European Search Report for European Patent Application No. 07255016.3-2218, Apr. 18, 2008, 6 pgs.

Gao, Nuo, Detecting Human Head Conductivity Distribution Using One Component Magnetic Flux Density, Sep. 2005, IEEE, pp. 1537-1539.

Prakash, N., Localization of a Magnetic Marker for GI Motility Studies: An In Vitro Feasibility Study, IEEE, 1007, pp. 2394-2397.

Raab, F., "Magnetic Position and Orientation Tracking System," 1979, IEEE, vol. 15, No. 5, pp. 709-717.

Schlageter, V., "Tracking system with five degrees of freedom using a 2D-array of Hall sensors and a permanent magnet," 2001, Elsevier, pp. 37-42.

Schlageter, V., Tracking system with five degrees of freedom using a 2D-array of Hall sensors and a permanent magnet, pp. 679-682, From the 14th European conference on Solid-State Transducers, Aug. 27-30, 2000, Copenhagen, Denmark, ISBN No. 87-89935-50-0.

Ybukami, S., "Motion Capture System of Magnetic Makers Using Three-Axial Magnetic Field Sensor," 2000, IEEE, vol. 36, No. 5, pp. 3646-3648.

Australian Office Action for Australian Patent Application No. 2006252293, May 18, 2010, 5 pgs.

Australian Office Action for Australian Patent Application No. 2006252294, Jun. 1, 2010, 2 pgs.

Australian Office Action for Australian Patent Application No. 2006252291, Apr. 13, 2011, 4 pgs.

European Search Report for European Patent Application No. 06256541.1-1265, Apr. 17, 2007, 9 pgs.

European Search Report for European Application No. 06256549.4-2318, May 10, 2007, 11 pgs.

European Search Report for European Application No. 06256574.2-1526, Feb. 12, 2008, 6 pgs.

European Search Report for European Patent Application No. 06256546.0-2310, Apr. 15, 2008, 7 pgs.

European Search Report for European Patent Application No. 06256546.0-2310/1803413, Jul. 16, 2008, 15 pgs.

Office Action for European Patent Application No. 06256549.4-2310, Jul. 13, 2009, 4 pgs.

* cited by examiner

_US 8,068,648 B2_

METHOD AND SYSTEM FOR REGISTERING A BONE OF A PATIENT WITH A COMPUTER ASSISTED ORTHOPAEDIC SURGERY SYSTEM

CROSS-REFERENCE TO RELATED U.S. PATENT APPLICATION

Cross-reference is made to U.S. Utility patent application Ser. No. 11/323,609 entitled "APPARATUS AND METHOD FOR REGISTERING A BONE OF A PATIENT WITH A COMPUTER ASSISTED ORTHOPAEDIC SURGERY SYSTEM," which was filed on Dec. 30, 2005 by Jason T. Sherman et al., to U.S. Utility patent application Ser. No. 11/323,610 entitled "MAGNETIC SENSOR ARRAY," which was filed on Dec. 30, 2005 by Jason T. Sherman et al., to U.S. Utility patent application Ser. No. 11/323,537entitled "METHOD FOR DETERMINING A POSITION OF A MAGNETIC SOURCE," which was filed on Dec. 30, 2005 by Jason T. Sherman et al., and to U.S. Utility patent application Ser. No. 11/323,963 entitled "SYSTEM AND METHOD FOR REGISTERING A BONE OF A PATIENT WITH A COMPUTER ASSISTED ORTHOPAEDIC SURGERY SYSTEM," which was filed on Dec. 30, 2005 by Jason T. Sherman et al., the entirety of each of which is expressly incorporated herein by reference.

TECHNICAL FIELD

The present disclosure relates generally to computer assisted surgery systems for use in the performance of orthopaedic surgical procedures and, more particularly, to methods and systems for registering a bone of a patient to a computer assisted orthopaedic surgery system.

BACKGROUND

There is an increasing adoption of minimally invasive orthopaedic procedures. Because such surgical procedures generally restrict the surgeon's ability to see the operative area, surgeons are increasingly relying on computer systems, such as computer assisted orthopaedic surgery (CAOS) systems, to assist in the surgical operation.

Computer assisted orthopaedic surgery (CAOS) systems assist surgeons in the performance of orthopaedic surgical procedures by, for example, displaying images illustrating surgical steps of the surgical procedure being performed and rendered images of the relevant bones of the patient. Before a computer assisted orthopaedic surgery (CAOS) system can display a rendered image of a bone, the bone must first be registered with the computer assisted orthopaedic surgery (CAOS) system. Registering the bone with the computer assisted orthopaedic surgery (CAOS) system allows the system to determine the relevant contour, location, and orientation of the bone and display the rendered image according to such parameters. In typical computer assisted orthopaedic surgery (CAOS) systems, a bone is registered by touching a number of locations of the bone with a probe. In response, the system computes a rendered image of the bone, including the contour of the bone, based on the recorded locations. Because the typical registration process occurs during the orthopaedic surgery procedure, the typical registration process adds additional surgery time and increases the time during which the patient is exposed to possible infection. Moreover, current registration of the bony anatomy of particular skeletal areas, such as the hip joint, are challenging due to the difficulty of repeatably locating fiducial markers and anatomical planes.

SUMMARY

According to one aspect, a method for registering a bone of a patient with a computer assisted orthopaedic surgery system may include retrieving an image of the bone. The image of the bone may include indicia of the position of a magnetic source coupled to the bone. The image of the bone defines an image coordinate system. The image may be, for example, a three-dimensional medical image of the bone of the patient. The method may also include determining the position of a reference array coupled to the bone of the patient. The reference array defines a bone coordinate system. The reference array may be, for example, a reflective optical reference array or a radio frequency reference array.

The method may further include determining first data indicative of the position of the magnetic source in the bone coordinate system. The position of the magnetic source may include the location of the centroid of the magnet in the bone coordinate system and the direction of a polar axis of the magnet in the bone coordinate system. To determine the first data, a magnetic sensor array may be positioned in a magnetic field generated by the magnetic source. The magnetic sensor array may define a magnetic sensor array coordinate system. The position of the magnetic source may be determined by measuring a magnetic flux density of the magnetic field at a plurality of points in space with a number of magnetic sensors of the magnetic sensor array. The position of the magnetic source may be determined in the magnetic sensor array coordinate system. For example, the location of the centroid of a magnet coupled to the bone may be determined in the magnetic sensor array coordinate system. Additionally, the direction of a polar axis of the magnet may be determined in the magnetic sensor array coordinate system. Further, the position of the magnetic sensor array in a global coordinate system defined by a tracking unit, such as a camera unit or wireless receiver, of the computer assisted orthopaedic surgery system may be determined. Additionally, the position of the bone of the patient in the global coordinate system may be determined. Such positions may be defined by a first and a second transformation matrix, respectively.

The method may further include determining second data indicative of a correlation between the image coordinate system and the bone coordinate system based on the first data. To do so, a transformation matrix may be determined. The transformation matrix may be determined by, for example, estimating a transformation matrix for transforming the image coordinate system to the bone coordinate system, transforming the position of the magnetic source from the image coordinate system to the bone coordinate system using the estimated transformation matrix, generating third data indicative of the transformed position of the magnetic source, calculating a difference between the first data and the third data, and repeating these steps until the difference between the first data and the third data is less than a predetermined minimum threshold value. To calculate the difference between the first data and the third data, a sum of the squared difference between the first data and the third data may be calculated. The method may also include displaying an image of the bone in a position determined based on the second data. For example, the image of the bone may be displayed in a location and orientation determined using the estimated transformation matrix.

According to another aspect, a system for registering a bone of a patient with a computer assisted orthopaedic surgery system may include a first reference array configured to be coupled to the bone of the patient. The first reference array may define a first coordinate system. The system may also include a display device, a processor electrically coupled to the display device, and a memory device electrically coupled to the processor. The memory device may have stored therein a plurality of instructions, which when executed by the processor, cause the processor to retrieve an image of the bone including indicia of the position of a magnetic source coupled to the bone. The image may define a second coordinate system. The plurality of instructions may also cause the processor to determine first data indicative of the position of the magnetic source in the first coordinate system. To do so, the processor may transform the position of the magnetic source from the second coordinate system to the first coordinate system. Additionally or alternatively, the processor may determine the location of the centroid of a magnet and a polar axis of the magnetic source in the first coordinate system. The system may also include a magnetic sensor array having a second reference array coupled thereto. The second reference array defines a third coordinate system. In such embodiments, the process may determine the position of the magnetic source in the third coordinate system using the magnetic sensor array.

The plurality of instructions may also cause the processor to determine second data indicative of a correlation between the second coordinate system and the first coordinate system based on the first data. To do so, the processor may be configured to determine a transformation matrix. For example, the processor may be configured to estimate a transformation matrix for transforming the image coordinate system to the bone coordinate system, transform the position of the magnetic source from the image coordinate system to the bone coordinate system using the estimated transformation matrix, generate third data indicative of the transformed position of the magnetic source, calculate a difference between the first data and the third data, and repeat these steps until the difference between the first data and the third data is less than a predetermined minimum threshold value. In addition, the plurality of instructions may also cause the processor to display an image of the bone on the display device in a position determined based on the second data.

According to a further aspect, a method for registering a bone of a patient with a computer assisted orthopaedic surgery system may include determining the position of a magnet coupled to the bone in a first coordinate system defined by a magnetic sensor array. To do so, the location of the centroid of the magnet and a polar axis of the magnet may be determined in the first coordinate system. The method may also include transforming the position of the magnet from the first coordinate system to a second coordinate system defined by a reference array coupled to the bone. The position of the magnet may be transformed by determining a first matrix defining the position of the magnetic sensor array in a fourth coordinate system defined by the computer assisted orthopaedic surgery system and determining a second matrix defining the position of the bone of the patient in the fourth coordinate system.

The method may also include generating first data indicative of the position of the magnet in the second coordinate system. The first data may include, for example, the location of the centroid of the magnet and the direction of a polar axis of the magnet in the second coordinate system. Additionally, the method may include retrieving an image of the bone having indicia of the position of the magnet. The image may define a third coordinate system.

The method may further include determining a transformation matrix for transforming the position of the magnet from the third coordinate system to the second coordinate system based on the first data. The transformation matrix may be determined by, for example, determining an estimated transformation matrix for transforming the third coordinate system to the second coordinate system, transforming the position of the magnetic source from the third coordinate system to the second coordinate system using the estimated transformation matrix, generating second data indicative of the transformed position of the magnetic source, calculating a difference between the first data and the second data, and repeating theses steps until the difference between the first data and the second data is less than a predetermined minimum threshold value. The difference between the first data and the second data may be determined by calculating a sum of the squared difference between the first data and the second data. The method may also include displaying an image of the bone in a location and orientation determined using the transformation matrix.

BRIEF DESCRIPTION OF THE DRAWINGS

The detailed description particularly refers to the following figures, in which.

DETAILED DESCRIPTION OF THE DRAWINGS

Figure 1:
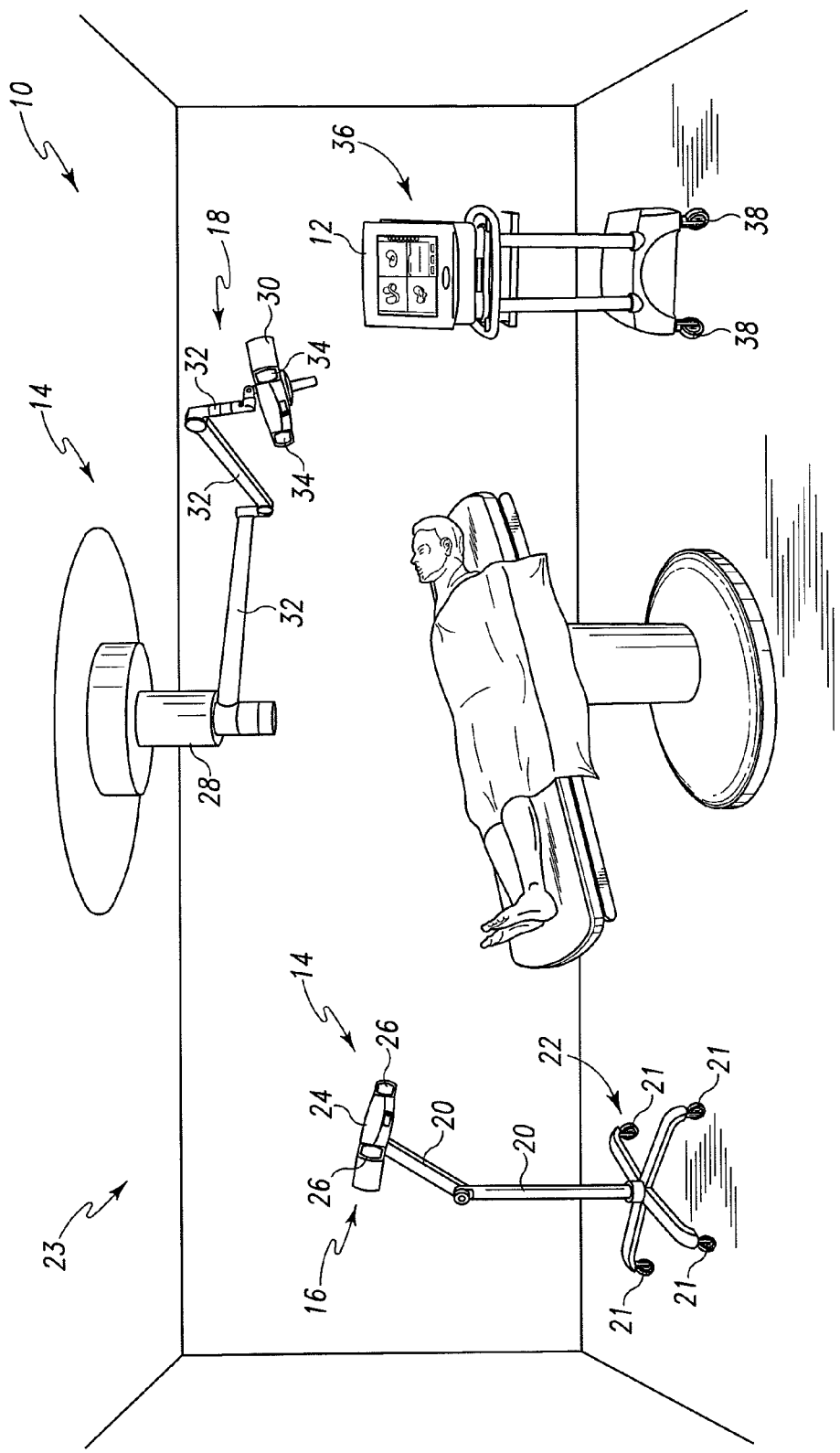
FIG. 1 is a perspective view of a computer assisted orthopaedic surgery (CAOS) system.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Referring to FIG. 1, a computer assisted orthopaedic surgery (CAOS) system 10 includes a computer 12 and a camera unit 14. The CAOS system 10 may be embodied as any type of computer assisted orthopaedic surgery system. Illustratively, the CAOS system 10 is embodied as one or more computer assisted orthopaedic surgery systems commercially available from DePuy Orthopaedics, Inc. of Warsaw, Ind. and/or one or more computer assisted orthopaedic surgery systems commercially available from BrainLAB of Fledkirchen, Germany.

The camera unit 14 may be embodied as a mobile camera unit 16 or a fixed camera unit 18. In some embodiments, the system 10 may include both types of camera units 16, 18. The mobile camera unit 16 includes a stand 20 coupled with a base 22. The base 22 may include a number of wheels 21 to allow the mobile camera unit 16 to be repositioned within a hospital room 23. The mobile camera unit 16 includes a camera head 24. The camera head 24 includes two cameras 26. The camera head 24 may be positionable relative to the stand 20 such that the field of view of the cameras 26 may be adjusted. The fixed camera unit 18 is similar to the mobile camera unit 16 and includes a base 28, a camera head 30, and an arm 32 coupling the camera head 30 with the base 28. In some embodiments, other peripherals, such as display screens, lights, and the like, may also be coupled with the base 28. The camera head 30 includes two cameras 34. The fixed camera unit 18 may be coupled to a ceiling, as illustratively shown in FIG. 1, or a wall of the hospital room. Similar to the camera head 24 of the camera unit 16, the camera head 30 may be positionable relative to the arm 32 such that the field of view of the cameras 34 may be adjusted. The camera units 14, 16, 18 are communicatively coupled with the computer 12. The computer 12 may be mounted on or otherwise coupled with a cart 36 having a number of wheels 38 to allow the computer 12 to be positioned near the surgeon during the performance of the orthopaedic surgical procedure.

Figure 2:
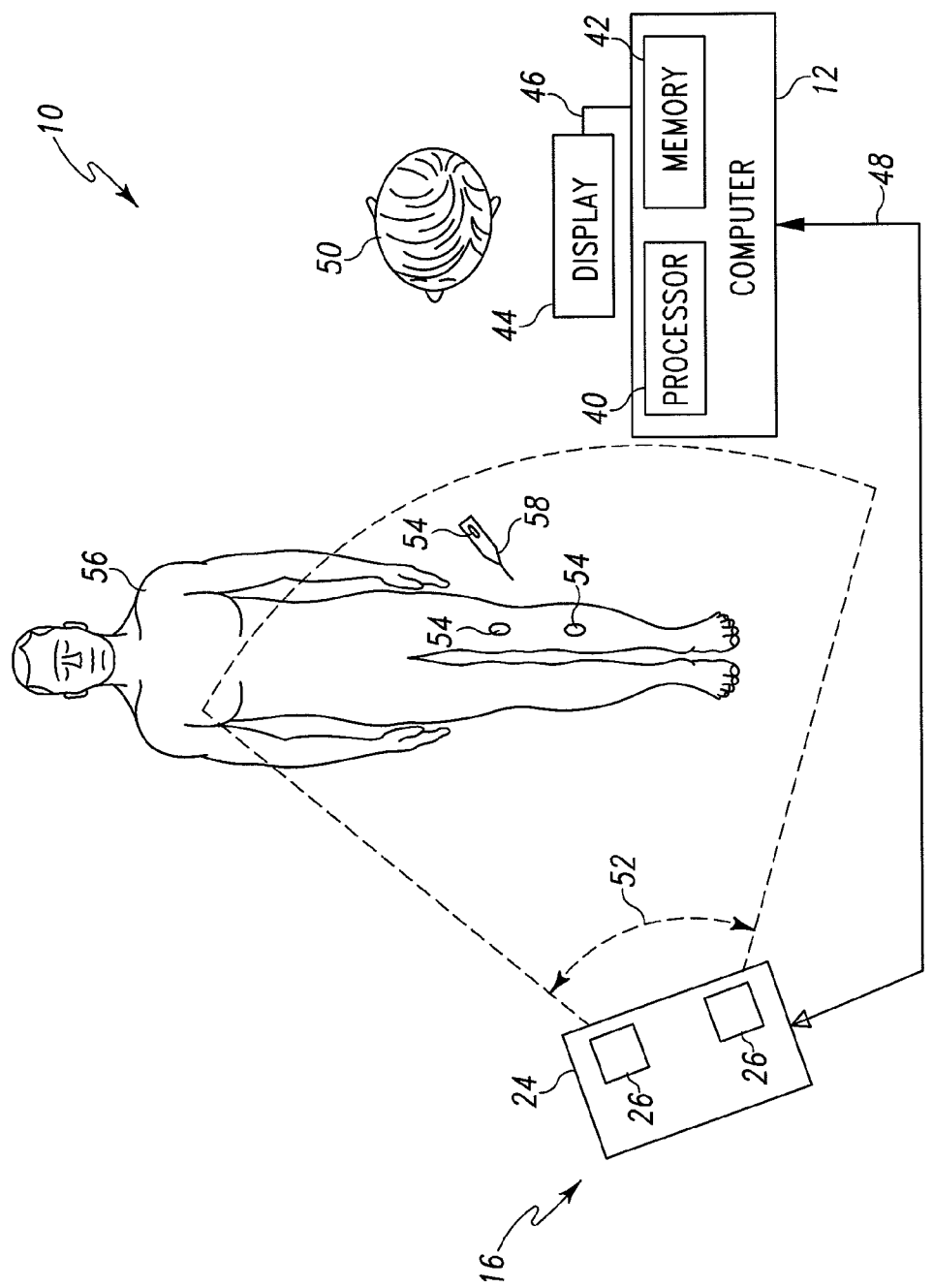
FIG. 2 is a simplified diagram of the CAOS system of FIG. 1.

Referring now to FIG. 2, the computer 12 illustratively includes a processor 40 and a memory device 42. The processor 40 may be embodied as any type of processor including, for example, discrete processing circuitry (e.g., a collection of logic devices), general purpose integrated circuit(s), and/or application specific integrated circuit(s) (i.e., ASICs). The memory device 42 may be embodied as any type of memory device and may include one or more memory types, such as, random access memory (i.e., RAM) and/or read-only memory (i.e., ROM). In addition, the computer 12 may include other devices and circuitry typically found in a computer for performing the functions described herein such as, for example, a hard drive, input/output circuitry, and the like.

The computer 12 is communicatively coupled with a display device 44 via a communication link 46. Although illustrated in FIG. 2 as separate from the computer 12, the display device 44 may form a portion of the computer 12 in some embodiments. Additionally, in some embodiments, the display device 44 or an additional display device may be positioned away from the computer 12. For example, the display device 44 may be coupled with the ceiling or wall of the operating room wherein the orthopaedic surgical procedure is to be performed. Additionally or alternatively, the display device 44 may be embodied as a virtual display such as a holographic display, a body mounted display such as a heads-up display, or the like. The computer 12 may also be coupled with a number of input devices such as a keyboard and/or a mouse for providing data input to the computer 12. However, in the illustrative embodiment, the display device 44 is a touch-screen display device capable of receiving inputs from an orthopaedic surgeon 50. That is, the surgeon 50 can provide input data to the computer 12, such as making a selection from a number of on-screen choices, by simply touching the screen of the display device 44.

The computer 12 is also communicatively coupled with the camera unit 16 (and/or 18) via a communication link 48. Illustratively, the communication link 48 is a wired communication link but, in some embodiments, may be embodied as a wireless communication link. In embodiments wherein the communication link 48 is a wireless signal path, the camera unit 16 and the computer 12 include wireless transceivers such that the computer 12 and camera unit 16 can transmit and receive data (e.g., image data). Although only the mobile camera unit 16 is shown in FIG. 2, it should be appreciated that the fixed camera unit 18 may alternatively be used or may be used in addition to the mobile camera unit 16.

Figure 3:
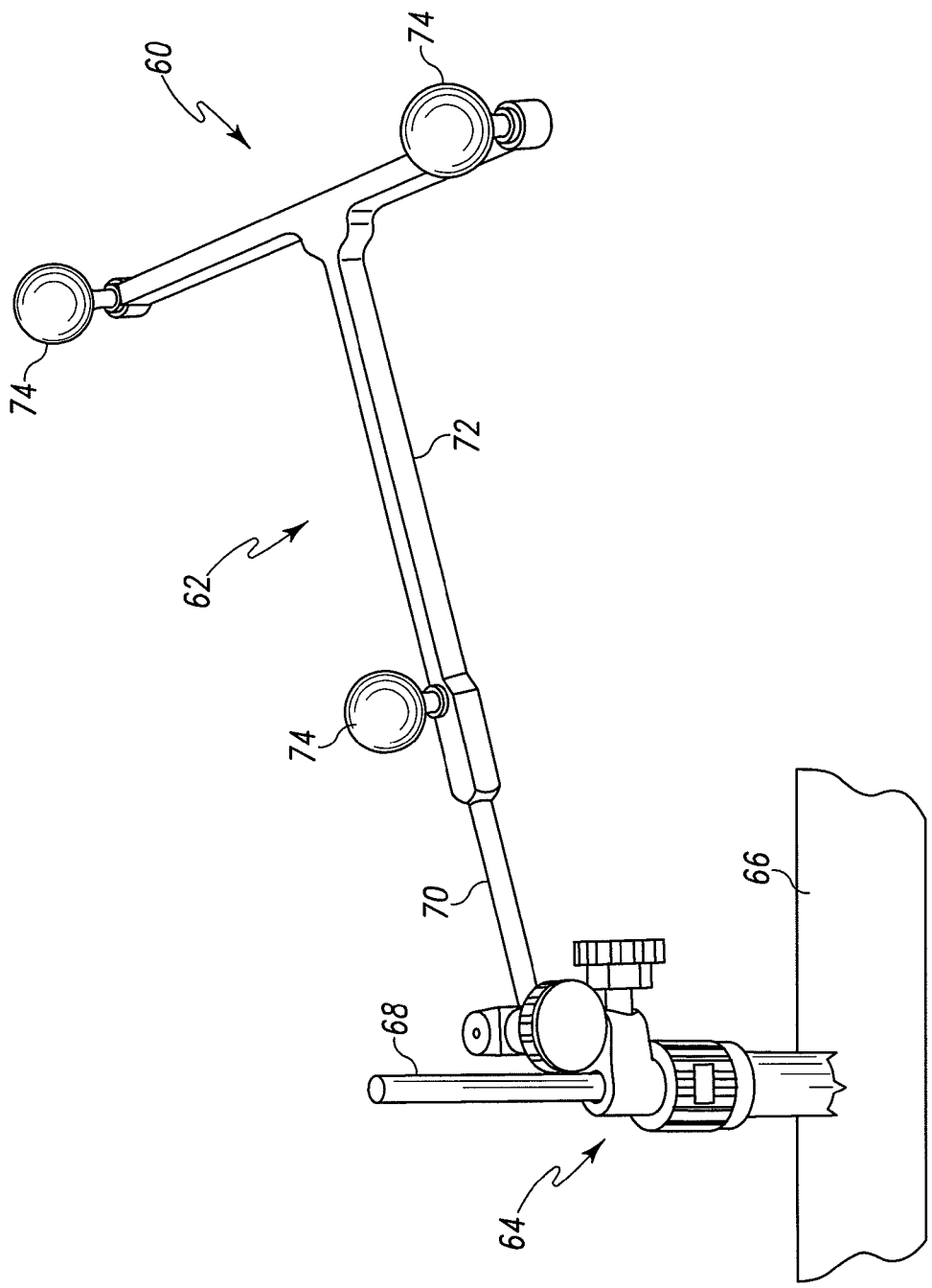
FIG. 3 is a perspective view of a bone locator tool.

The CAOS system 10 may also include a number of sensor or reference arrays 54, which may be coupled the relevant bones of a patient 56 and/or with orthopaedic surgical tools 58. For example, as illustrated in FIG. 3, a tibial array 60 includes a reference array 62 and bone clamp 64. The illustrative bone clamp 64 is configured to be coupled with a tibia bone 66 of the patient 56 using a Schantz pin 68, but other types of bone clamps may be used. The reference array 62 is coupled with the bone clamp 64 via an extension arm 70. The reference array 62 includes a frame 72 and three reflective elements or sensors 74. The reflective elements 74 are embodied as spheres in the illustrative embodiment, but may have other geometric shapes in other embodiments. Additionally, in other embodiments reference arrays having more than three reflective elements may be used. The reflective elements 74 are positioned in a predefined configuration that allows the computer 12 to determine the identity of the tibial array 60 based on the configuration. That is, when the tibial array 60 is positioned in a field of view 52 of the camera head 24, as shown in FIG. 2, the computer 12 is configured to determine the identity of the tibial array 60 based on the images received from the camera head 24. Additionally, based on the relative position of the reflective elements 74, the computer 12 is configured to determine the location and orientation of the tibial array 60 and, accordingly, the tibia 66 to which the array 60 is coupled.

Figure 4:
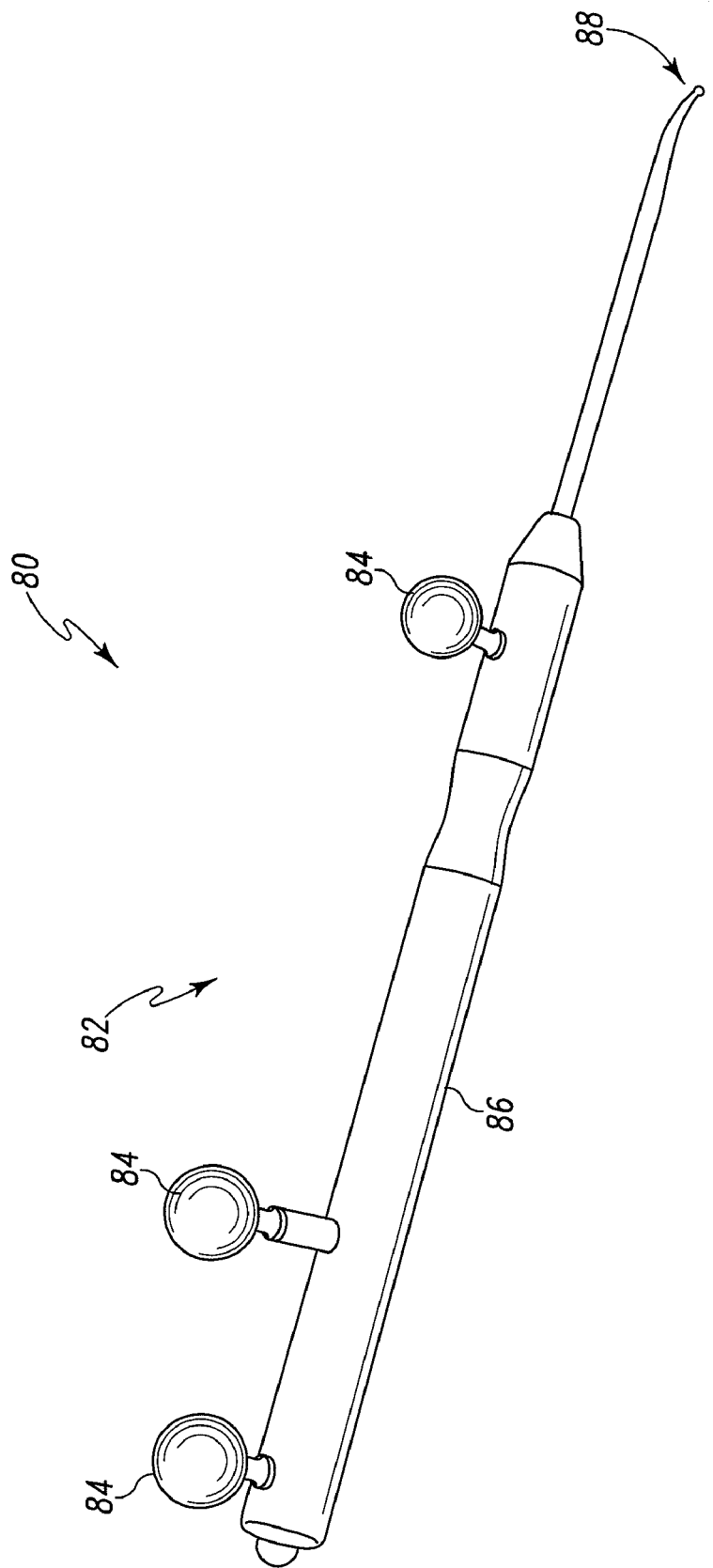
FIG. 4 is a perspective view of a registration tool for use with the system of FIG. 1.
Figure 5:
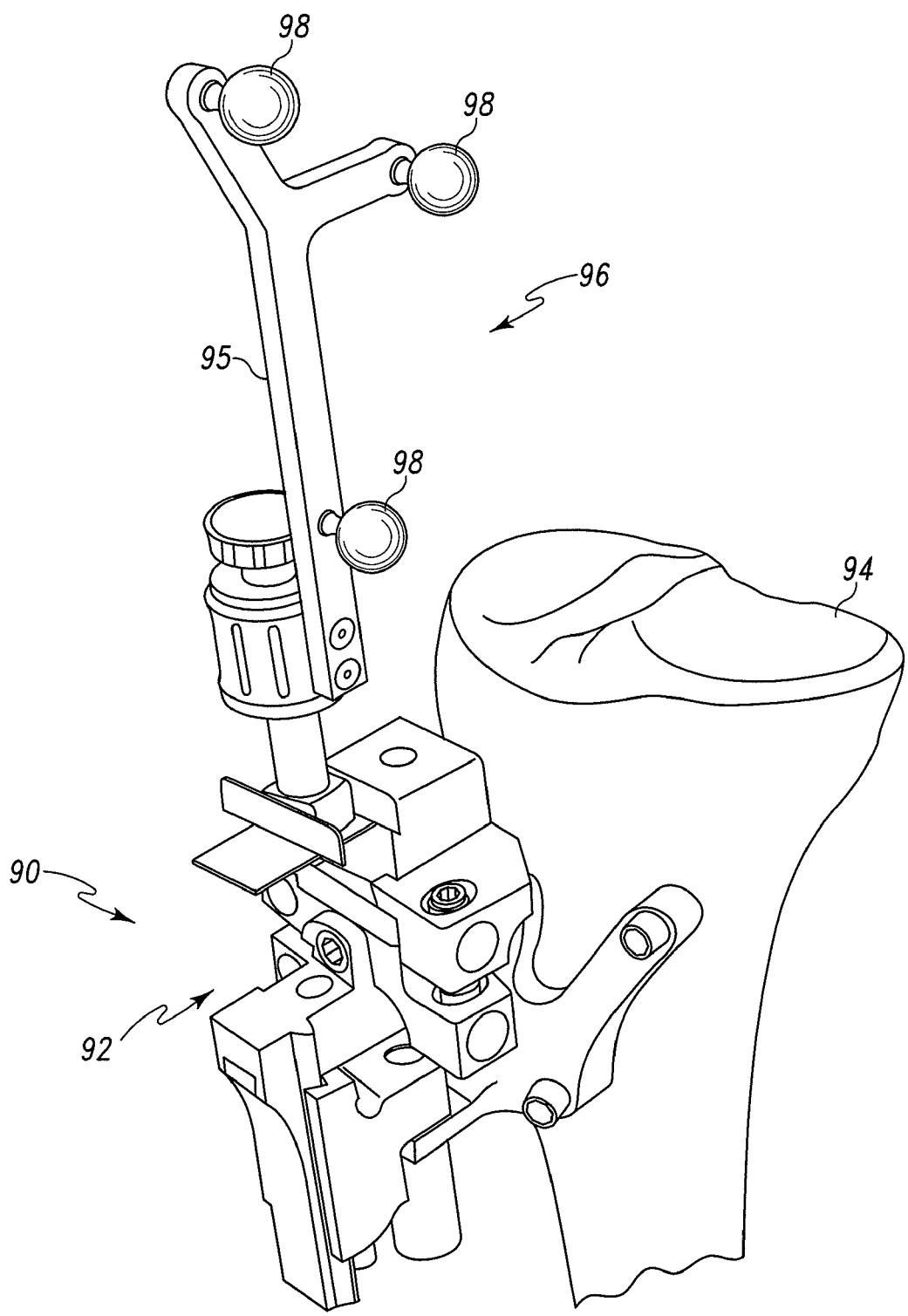
FIG. 5 is a perspective view of an orthopaedic surgical tool for use with the system of FIG. 1.

Reference arrays may also be coupled to other surgical tools. For example, a registration tool 80, as shown in FIG. 4, is used to register points of a bone as discussed in more detail below in regard to FIG. 7. The registration tool 80 includes a reference array 82 having three reflective elements 84 coupled with a handle 86 of the tool 80. The registration tool 80 also includes pointer end 88 that is used to register points of a bone. The reflective elements 84 are also positioned in a configuration that allows the computer 12 to determine the identity of the registration tool 80 and its relative location (i.e., the location of the pointer end 88). Additionally, reference arrays may be used on other surgical tools such as a tibial resection jig 90, as illustrated in FIG. 5. The jig 90 includes a resection guide portion 92 that is coupled with a tibia bone 94 at a location of the bone 94 that is to be resected. The jig 90 includes a reference array 96 that is coupled with the portion 92 via a frame 95. The reference array 96 includes three reflective elements 98 that are positioned in a configuration that allows the computer 12 to determine the identity of the jig 90 and its relative location (e.g., with respect to the tibia bone 94).

The CAOS system 10 may be used by the orthopaedic surgeon 50 to assist in any type of orthopaedic surgical procedure including, for example, a total knee replacement procedure. To do so, the computer 12 and/or the display device 44 are positioned within the view of the surgeon 50. As discussed above, the computer 12 may be coupled with a movable cart 36 to facilitate such positioning. The camera unit 16 (and/or camera unit 18) is positioned such that the field of view 52 of the camera head 24 covers the portion of a patient 56 upon which the orthopaedic surgical procedure is to be performed, as shown in FIG. 2.

During the performance of the orthopaedic surgical procedure, the computer 12 of the CAOS system 10 is programmed or otherwise configured to display images of the individual surgical procedure steps that form the orthopaedic surgical procedure being performed. The images may be graphically rendered images or graphically enhanced photographic images. For example, the images may include three-dimensional rendered images of the relevant anatomical portions of a patient. The surgeon 50 may interact with the computer 12 to display the images of the various surgical steps in sequential order. In addition, the surgeon 50 may interact with the computer 12 to view previously displayed images of surgical steps, selectively view images, instruct the computer 12 to render the anatomical result of a proposed surgical step or procedure, or perform other surgical related functions. For example, the surgeon 50 may view rendered images of the resulting bone structure of different bone resection procedures. In this way, the CAOS system 10 provides a surgical "walk-through" for the surgeon 50 to follow while performing the orthopaedic surgical procedure.

In some embodiments, the surgeon 50 may also interact with the computer 12 to control various devices of the system 10. For example, the surgeon 50 may interact with the system 10 to control user preferences or settings of the display device 44. Further, the computer 12 may prompt the surgeon 50 for responses. For example, the computer 12 may prompt the surgeon 50 to inquire if the surgeon 50 has completed the current surgical step, if the surgeon 50 would like to view other images, and the like.

The camera unit 16 and the computer 12 also cooperate to provide the surgeon 50 with navigational data during the orthopaedic surgical procedure. That is, the computer 12 determines and displays the location of the relevant bones and the surgical tools 58 based on the data (e.g., images) received from the camera head 24 via the communication link 48. To do so, the computer 12 compares the image data received from each of the cameras 26 and determines the location and orientation of the bones and tools 58 based on the relative location and orientation of the reference arrays 54, 62, 82, 96. The navigational data displayed to the surgeon 50 is continually updated. In this way, the CAOS system 10 provides visual feedback of the locations of relevant bones and surgical tools for the surgeon 50 to monitor while performing the orthopaedic surgical procedure.

Figure 6:
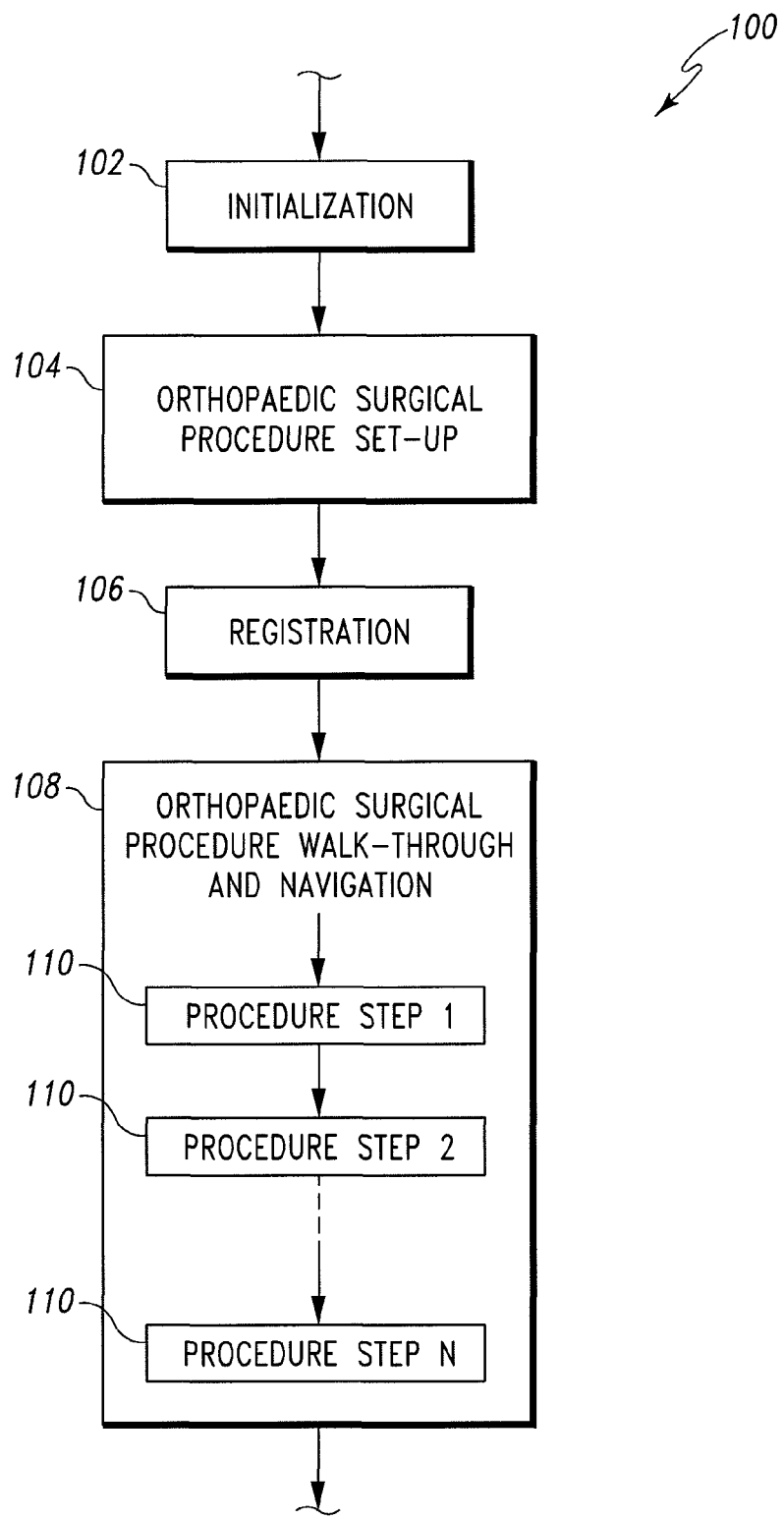
FIG. 6 is a simplified flowchart diagram of an algorithm that is used by the CAOS system of FIG. 1.

Referring now to FIG. 6, an algorithm 100 for assisting a surgeon 50 in performing an orthopaedic surgical procedure is executed by the computer 12. The algorithm 100 begins with a process step 102 in which the CAOS system 10 is initialized. During process step 102, settings, preferences, and calibrations of the CAOS system 10 are established and performed. For example, the video settings of the display device 44 may be selected, the language displayed by the computer 12 may be chosen, and the touch screen of the display device 44 may be calibrated in process step 102.

In process step 104, the selections and preferences of the orthopaedic surgical procedure are chosen by the surgeon 50. Such selections may include the type of orthopaedic surgical procedure that is to be performed (e.g., a total knee arthroplasty), the type of orthopaedic implant that will be used (e.g., make, model, size, fixation type, etc.), the sequence of operation (e.g., the tibia or the femur first), and the like. Once the orthopaedic surgical procedure has been set up in process step 104, the bones of the patient 56 are registered in process step 106. To do so, reference arrays, such as the tibial array 60 illustrated in FIG. 3, are coupled with the relevant bones of the patient (i.e., the bones involved in the orthopaedic surgical procedure). Additionally, the contours of such bones are registered using the registration tool 80. To do so, the pointer end 88 of the tool 80 is touched to various areas of the bones to be registered. In response to the registration, the computer 12 displays rendered images of the bones wherein the location and orientation of the bones are determined based on the reference arrays coupled therewith and the contours of the bones are determined based on the registered points. Because only a selection of the points of the bone is registered, the computer 12 calculates and renders the remaining areas of the bones that are not registered with the tool 80.

Once the pertinent bones have been registered in process step 106, the computer 12, in cooperation with the camera unit 16, 18, displays the images of the surgical steps of the orthopaedic surgical procedure and associated navigation data (e.g., location of surgical tools) in process step 108. To do so, the process step 108 includes a number of sub-steps 110 in which each surgical procedure step is displayed to the surgeon 50 in sequential order along with the associated navigational data. The particular sub-steps 110 that are displayed to the surgeon 50 may depend on the selections made by the surgeon 50 in the process step 104. For example, if the surgeon 50 opted to perform a particular procedure tibia-first, the sub-steps 110 are presented to the surgeon 50 in a tibia-first order Referring now to FIG. 7, in another embodiment, a system 200 for pre-operatively registering a bone or bony anatomy (i.e., one or more bones) of a patient includes a computer assisted orthopaedic surgery (CAOS) system 202, a magnetic sensor array 204, and one or more magnetic sources 206. The computer assisted orthopaedic surgery (CAOS) system 202 includes a controller 208, a camera unit 210, and a display device 212. The controller 208 is communicatively coupled with the camera unit 210 via a communication link 214. The communication link 214 may be any type of communication link capable of transmitting data (i.e., image data) from the camera unit 210 to the controller 208. For example, the communication link 214 may be a wired or wireless communication link and use any suitable communication technology and/or protocol to transmit the image data.

In the illustrative embodiment, the camera unit 210 is similar to and operates in a similar manner as the camera unit 16 of the system 10 described above in regard to FIG. 1. For example, the camera unit 210 includes a camera head 216 having a number of cameras (not shown) and may be used in cooperation with the controller 208 to determine the location and orientation of one or more reference arrays 218 positioned in the field of view of the camera unit 210, as discussed in detail above in regard to the camera unit 16. The reference arrays 218 may be embodied as optical reference arrays similar to the reference arrays 54, 62, 82, 96 illustrated in and described above in regard to FIGS. 2-4 and, as such, may include a number of reflective elements. The reference arrays 218 may be coupled with bones of the a patient and/or various medical devices, such as probes, saw guides, ligament balancers, and the like, used during the orthopaedic surgical procedure. Alternatively, in other embodiments, other types of tracking units may be used. For example, in some embodiments, the camera unit 210 may be replaced or supplemented with a wireless receiver (which may be included in the controller 208 in some embodiments) and the reference arrays 218 may be embodied as wireless transmitters (e.g., electromagnetic transmitters). Additionally, the medical devices may be embodied as "smart" medical devices such as, for example, smart surgical instruments, smart surgical trials, smart surgical implants, and the like. In such embodiments, the controller 208 is configured to determine the location of the medical devices based on wireless data signals received from the smart medical devices.

The controller 208 is communicatively coupled with the display device 212 via a communication link 220. Although illustrated in FIG. 7 as separate from the controller 208, the display device 212 may form a portion of the controller 208 in some embodiments. Additionally, in some embodiments, the display device 212 may be positioned away from the controller 208. For example, the display device 212 may be coupled with a ceiling or wall of the operating room wherein the orthopaedic surgical procedure is to be performed. Additionally or alternatively, the display device 212 may be embodied as a virtual display such as a holographic display, a body mounted display such as a heads-up display, or the like. The controller 208 may also be coupled with a number of input devices such as a keyboard and/or a mouse. However, in the illustrative embodiment, the display device 212 is a touch-screen display device capable of receiving inputs from the surgeon 50 using the CAOS system 202. That is, the surgeon 50 can provide input data to the display device 212 and controller 208, such as making a selection from a number of on-screen choices, by simply touching the screen of the display device 212.

The controller 208 may be embodied as any type of controller including, but not limited to, a computer such as a personal computer, a specialized microcontroller device, a collection of processing circuits, or the like. The controller 208 includes a processor 222 and a memory device 224. The processor 222 may be embodied as any type of processor including, but not limited to, discrete processing circuitry and/or integrated circuitry such as a microprocessor, a microcontroller, and/or or an application specific integrated circuit (ASIC). The memory device 224 may include any number of memory devices and any type of memory such as random access memory (RAM) and/or read-only memory (ROM). Although not shown in FIG. 7, the controller 208 may also include other circuitry commonly found in a computer system.

The controller 208 may also include a database 226. The database 226 may be embodied as any type of database, electronic library, and/or file storage location. For example, the database 226 may be embodied as a structured database or as an electronic file folder or directory containing a number of separate files and an associated "look-up" table. Further, the database 226 may be stored on any suitable device. For example, the database 226 may be stored in a set of memory locations of, for example, the memory device 226 and/or a stored on a separate storage device such as a hard drive or the like.

Additionally or alternatively, the controller 208 may be coupled to a remote database 228 via a communication link 230. The remote database 228 may be similar to the database 226 and may be embodied as any type of database, electronic library, and/or a file storage location. The remote database 228 may be located apart from the controller 208. For example, the controller 208 may be located in an orthopaedic surgery room while the remote database 228 may form a part of a hospital network and be located in a separate room or building apart from the orthopaedic surgery room. As such, the communication link 230 may be embodied as any type of communication link capable of facilitating data transfer between the controller 208 and the remote database 228. For example, in some embodiments, the communication link 322 may form a portion of a network such as a Local Area Network (LAN), a Wide Area Network (WAN), and/or a global, publicly-accessible network such as the Internet. In use, the database(s) 226, 228 is accessed by the controller 208 to store and/or retrieve images of a bone(s) of a patient as discussed in more detail in regard to FIGS. 11 and 12.

The controller 208 also includes a receiver or transceiver 232. The receiver 232 is used by the processor 222 to communicate with the magnetic sensor array 204 via a communication link 234. The communication link 234 may be embodied as any type of communication link capable of transmitting data from the magnetic sensor array 204 to the controller 208. For example, the communication link 234 may be a wired or wireless communication link and use any suitable communication technology and/or protocol to transmit the data. As such, the receiver 232 may be embodied as any type of receiver capable of facilitating communication between the controller 208 and the magnetic sensor array 204 including, for example, a wired or wireless receiver.

Figure 7:
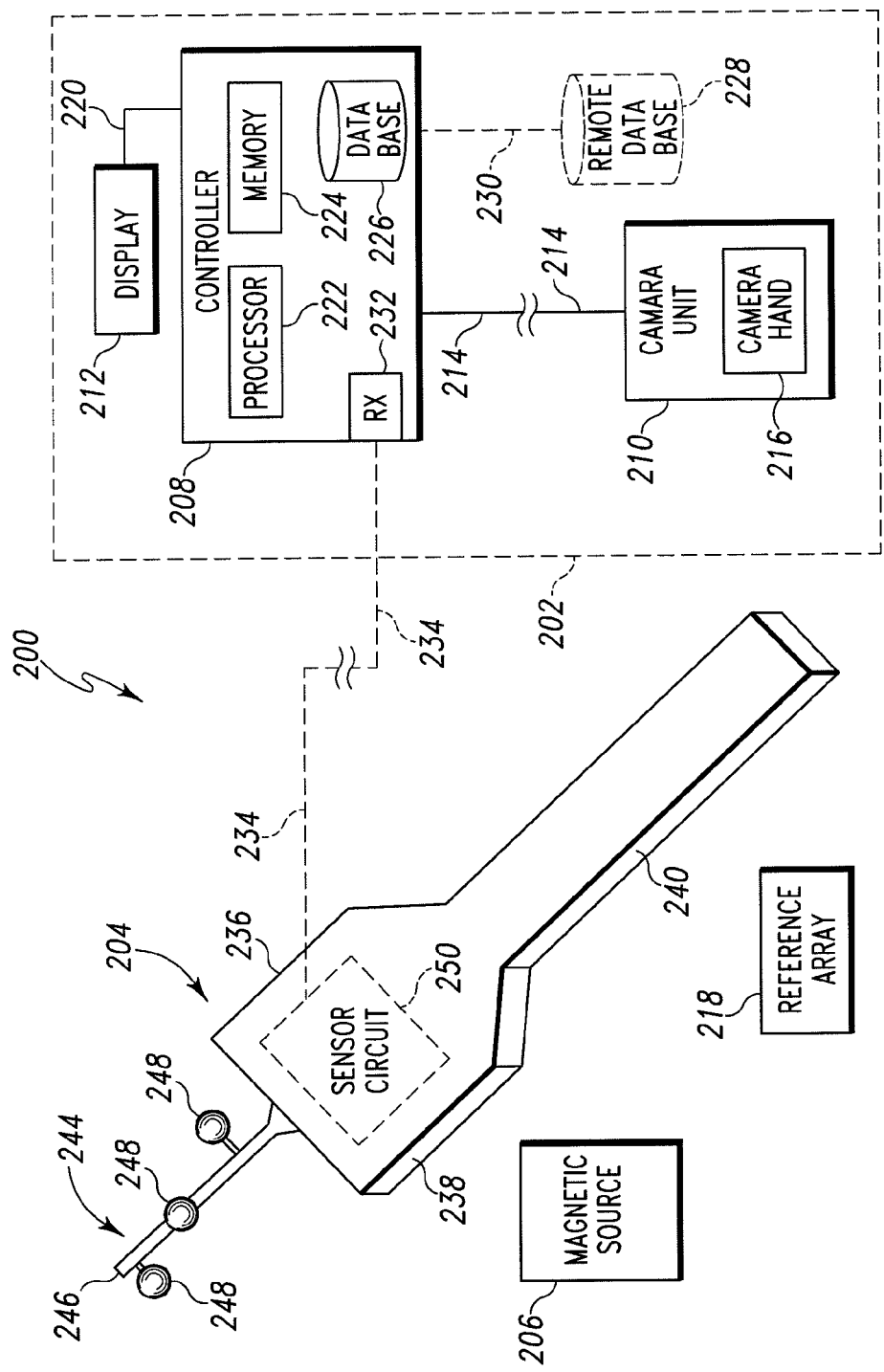
FIG. 7 is a simplified diagram of another CAOS system including a magnetic sensor array.

The illustrative magnetic sensor array 204 of FIG. 7 includes a housing 236 having a sensing head portion 238 and a handle 240 coupled to the head portion 238. The handle 240 may be used by a user of the system 200, such as an orthopaedic surgeon 50, to move and position the magnetic sensor array 204. The magnetic sensor array 204 also includes a sensor circuit 250 located in the head portion 238. As discussed in more detail below in regard to FIGS. 8 and 9, the sensor circuit 250 is configured to sense a magnetic field generated by the magnetic source 206 and determine data indicative of a position of the magnetic source 206 relative to the magnetic sensor array 204 and transmit such data via the communication link 234 and receiver 232 to the controller 208. It should be understood that, as used herein, the term "position" is intended to refer to any one or more of the six degrees of freedom that define the location and orientation of a body (e.g., the magnetic source 206) in space or relative to a predetermined point or other body.

In some embodiments, the magnetic sensor array 204 may also include an reflective reference array 244. The reflective reference array 244 includes a support frame 246 and a number of reflective sensor elements 248. The reflective reference array 244 is similar to the reference arrays 54, 62, 82, 96 described above in regard to FIGS. 2, 3, 4, and 5, respectively. The reflective sensor elements 248 are positioned in a predefined configuration that allows the controller 208 to determine the identity and position (i.e., three dimensional location and orientation) of the magnetic sensor array 204 based on the configuration. That is, when the magnetic sensor array 204 is positioned in the field of view of the camera unit 210, the controller 208 is configured to determine the identity and position of the magnetic sensor array 204 relative to the camera 210 and/or controller 208 based on the images received from the camera unit 210 via the communication link 214. In other embodiments, the reflective reference array 244 may replaced or complimented with a wireless transmitter. In such embodiments, the controller 208 includes a wireless receiver and is configured to determine the position and identity of the magnetic sensor array based on transmitted data received from the wireless transmitter.

Figure 8:
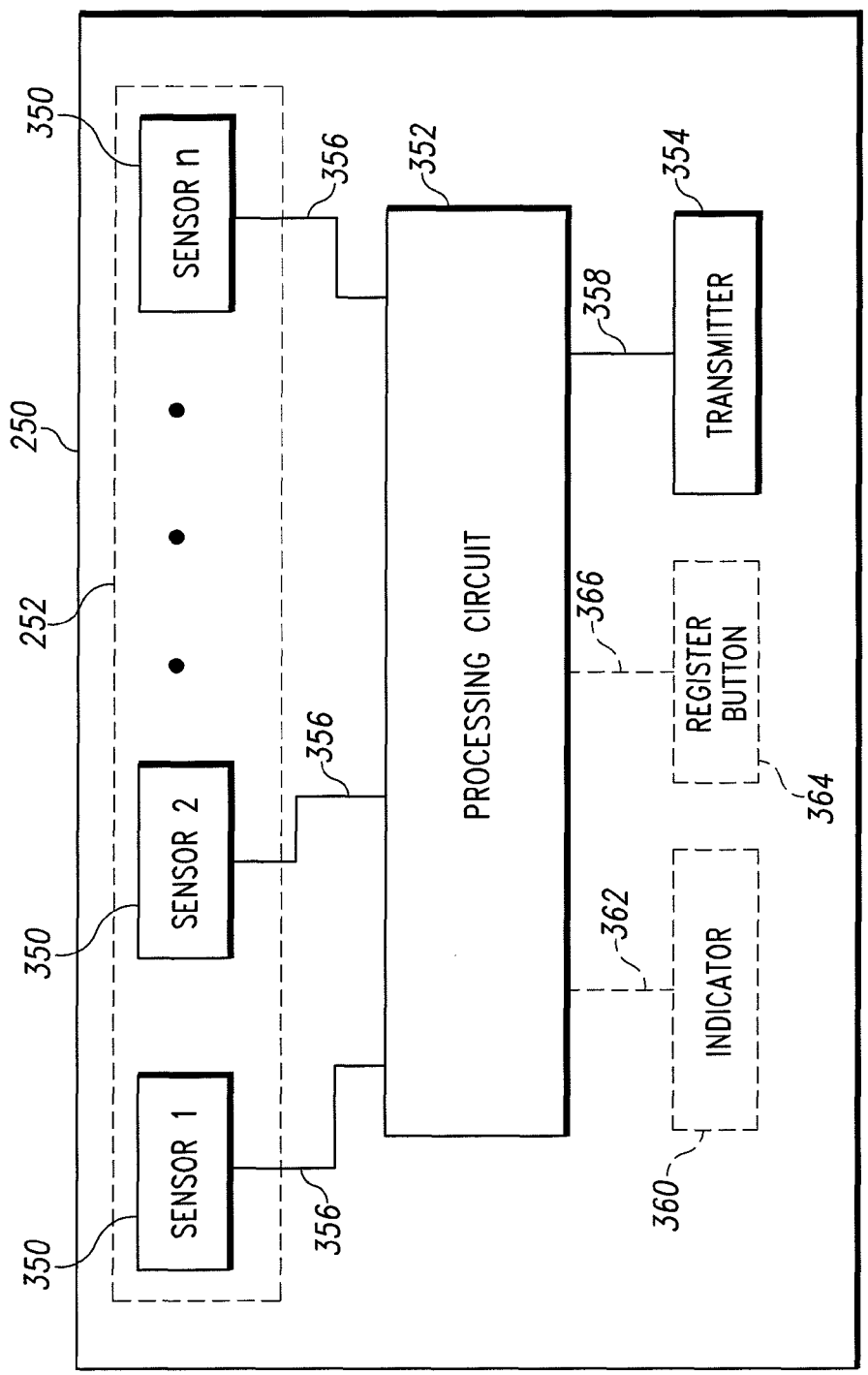
FIG. 8 is a simplified circuit diagram of one embodiment of a sensor circuit of the magnetic sensor array of FIG. 7.

To sense the magnetic field(s) of the magnetic source 206, the sensor circuit 250 includes a magnetic sensor arrangement 252 as illustrated in FIG. 8. The magnetic sensor arrangement 252 includes one or more magnetic sensors 350. The sensor circuit 250 also includes a processing circuit 352 and a transmitter 354. The magnetic sensors 350 are electrically coupled to the processing circuit 352 via a number of interconnects 356. The processing circuit 352 is also electrically coupled to the transmitter 354 via an interconnect 358. The interconnects 356, 358 may be embodied as any type of interconnects capable of providing electrical connection between the processing circuit 352, the sensors 350, and the transmitter 354 such as, for example, wires, cables, PCB traces, or the like.

The number of magnetic sensors 350 that form the magnetic sensor arrangement 252 may depend on such criteria as the type of magnetic sensors used, the specific application, and/or the configuration of the magnetic sensor array 204. For example, the magnetic sensors 350 are configured to measure a three-dimensional magnetic field of the magnetic source 206. As such, the sensor circuit 250 may include any number and configuration of one-dimensional, two-dimensional, and/or three-dimensional magnetic sensors such that the sensor circuit 252 is capable of sensing or measuring the magnetic field of the magnetic source 206 in three dimensions. Additionally, the magnetic sensor(s) 350 may be embodied as any type of magnetic sensor capable of sensing or measuring the magnetic field generated by the magnetic source 206. For example, the magnetic sensors 350 may be embodied as superconducting quantum interference (SQUID) magnetic sensors, anisotropic magnetoresistive (AMR) magnetic sensors, giant magnetoresistive (GMR) magnetic sensors, Hall-effect magnetic sensors, or any other type of magnetic sensors capable of sensing or measuring the three-dimensional magnetic field of the magnetic source. In one particular embodiment, the magnetic sensor(s) are embodied as X-H3X-xx_E3C-25HX-2.5-0.2T Three Axis Magnetic Field Transducers, which are commercially available from SENIS GmbH, of Zurich, Switzerland. Regardless, the magnetic sensors 350 are configured to produce a number of data values (e.g., voltage levels) which define one or more of the components (e.g., X—, Y—, and Z-components) of the three-dimensional magnetic flux density of the magnetic field of the magnetic source 206 at the point in space where each sensor is located and in the orientation of each sensor's active sensing element. These data values are transmitted to the processing circuit 352 via the interconnects 356.

Figure 9:
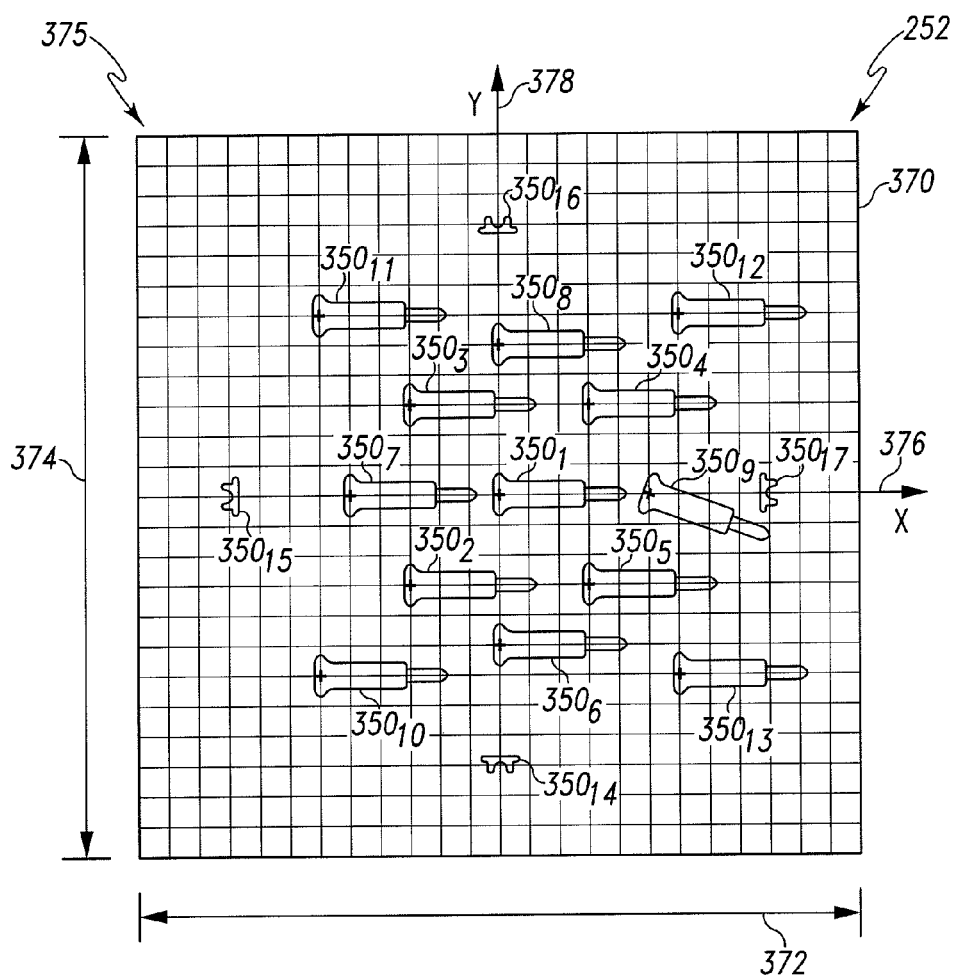
FIG. 9 is a plan view of one embodiment of a magnetic sensor arrangement of the sensor circuit of FIG. 8.

In one particular embodiment, the magnetic sensor arrangement 252 includes seventeen magnetic sensors $350_1$-$350_{17}$ configured as illustrated in FIG. 9. The magnetic sensors $350_1$-$350_{17}$ are secured to a sensor board 370. The sensor board 370 may be formed from any non-magnetic material capable of supporting the magnetic sensors $350_1$-$350_{17}$ in the desired configuration. For example, in the illustrative embodiment, the sensor board 370 is formed from FR4. The magnetic sensors $350_1$-$350_{17}$ may be mounted on or in the sensor board 370. As such, the sensor board 370 forms the sensing face of the sensor circuit 250 and may be located inside the head portion 332 of the magnetic sensor array 204 (i.e., located behind the housing material) or mounted to the head portion 332 such that the sensor board 370 is exposed.

The illustrative sensor board 370 has a width 372 of about 12 centimeters, a length 374 of about 12 centimeters, and a thickness (not shown) of about 1.25 centimeters. However, sensor boards having other dimensions that allow the mounting of the desired number of magnetic sensors 350 may be used. The magnetic sensors 350 are mounted to or in the sensor board 370 according to a predetermined configuration. For clarity of description, a grid 375 having an X-axis 376 and a Y-axis 378 is illustrated over the sensor board 370 in FIG. 9. In the illustrative embodiment, each unit of the grid 375 has a measurement of about 5 millimeters. Each of the magnetic sensors $350_1$-$350_{17}$ may be a one dimensional, two dimensional, or three dimensional sensor. As such, each of the magnetic sensors $350_1$-$350_{17}$ may include one, two, or three active sensing elements, respectively. Each sensing element of the magnetic sensors $350_1$-$350_{17}$ is capable of measuring at least one component of the magnetic flux density of a magnetic source at the position (i.e., location and orientation) of the particular magnetic sensor. To do so, each magnetic sensor 350 includes a field sensitive point, denoted as a "+" in FIG. 9, wherein the magnetic flux density is measured. The configuration of the magnetic sensors $350_1$-$350_{17}$ will be described below in reference to the field sensitive point of each magnetic sensor with the understanding that the body of the sensor may be positioned in numerous orientations wherein each orientation facilitates the same location of the field sensitive point.

As illustrated in FIG. 9, the first magnetic sensor $350_1$ is located at a central point (0, 0) on the grid 375. The first magnetic sensor $350_1$ is a three-dimensional magnetic sensor having three channels and generates data values (i.e., voltage levels) indicative of the X-, Y-, and Z-components of the measured magnetic flux density at the position of the sensor $350_1$. Four additional three-dimensional magnetic sensors $350_2$-$350_5$ are positioned around the first magnetic sensor $350_1$. The magnetic sensor $350_2$ is located at point (−15, 15), the magnetic sensor $350_3$ is located at point (−15, 15), the magnetic sensor $350_4$ is located at point (15, 15), and the magnetic sensor $350_5$ is located at point (15, −15), wherein each graduation mark of the grid 375 is defined as 5 units (e.g., 5 millimeters).

The magnetic sensor arrangement 252 also includes a number of single-dimensional magnetic sensors $350_6$-$350_{17}$. The magnetic sensors $350_6$-$350_{13}$ are positioned on the sensor board 370 such that the sensors $350_6$-$350_{13}$ measure the Z-component of the measured magnetic flux density (i.e., the magnetic flux generated by the magnetic source 206). In particular, the magnetic sensor $350_6$ is located at point (0, −25), the magnetic sensor $350_7$ is located at point (−25, 0), the magnetic sensor $350_8$ is located at point (0, 25), the magnetic sensor $350_9$ is located at point (25, 0), the magnetic sensor $350_{10}$ is located at point (−30, −30), the magnetic sensor $350_{11}$ is located at point (−30, 30), the magnetic sensor $350_{12}$ is located at point (30, 30), and the magnetic sensor $350_{13}$ is located at point (30, −30).

Conversely, the one-dimensional magnetic sensors $350_{14}$, $350_{16}$, and the magnetic sensors $350_{15}$, $350_{17}$ are positioned on the sensor board 370 such that the one-dimensional sensors $350_{14}$, $350_{16}$ and $350_{15}$, $350_{17}$ measure the magnitude of the Y-axis and X-axis components of the magnetic flux density of the measured magnetic field, respectively. In particular, the magnetic sensor $350_{14}$ is located at point (0,−45), the magnetic sensor $350_{15}$ is located at point (−45, 0), the magnetic sensor $350_{16}$ is located at point (0, 45), and the magnetic sensor $350_{17}$ is located at point (45, 0). As illustrated in FIG. 9, the magnetic sensors $350_{14}$-$350_{17}$ are positioned in or embedded in the sensor board 370 such that the magnetic sensors $350_{14}$-$350_{17}$ are positioned orthogonally to the measurement surface of the sensor board 370. Conversely, the magnetic sensors $350_1$-$350_{13}$ are positioned on the sensor board 370 coplanar with the measurement surface of the sensor board 370 or otherwise substantially parallel therewith.

In some embodiments, the magnetic sensors 350 may have differing magnetic field sensitivities (i.e., the ability to detect a change in the measured magnetic flux density) and sensing ranges. For example, in some embodiments, the magnetic sensors 350 located toward a central location of the sensor board 370 may have a lower magnetic field sensitivity but a greater sensing range than the magnetic sensors 350 located farther from the central location. In the illustrative embodiment of FIG. 9, the three-dimensional magnetic sensors $350_1$-$350_5$, which are located toward the center of the sensor board 370, have a lower magnetic field sensitivity and a greater sensing range than the one-dimensional magnetic sensors $350_6$-$350_{17}$ For example, in one particular embodiment, the three-dimensional magnetic sensors $350_1$-$350_5$ have a magnetic sensitivity of about 50 µT (micro-Tesla) and a sensing range of about 20 mT (milli-Tesla) while the one-dimensional magnetic sensors $350_6$-$350_{17}$ have a magnetic sensitivity of about 5 µT and a sensing range of about 2 mT. However, in other embodiments, there may be additional levels or differences of magnetic sensitivity and/or sensing range based on the particular distance of each magnetic source 350 from a predetermined location on the sensor board 370.

Because of such differences in magnetic field sensitivity and sensing range of the magnetic field sensors 350, the magnetic sensor arrangement 252 may be less susceptible to positioning variances of the magnetic sensor array 204 and/or the accuracy of the magnetic flux density measurements may be improved by having magnetic sensors 350 capable of measuring the magnetic flux density of the magnetic source 206 while the magnetic sensor array is positioned close to the magnetic source 206 without going into saturation. Additionally, the magnetic sensor arrangement 252 may be less susceptible to positioning variances of the magnetic sensor array 204 and/or the accuracy of the magnetic flux density measurements may be improved by having magnetic sensors 350 capable of measuring the magnetic field of the magnetic source 206 while the magnetic sensor array 204 is positioned far from the magnetic source 206 in spite of the increase in magnetic "noise" (i.e., undesirable magnetic field effects from sources other than the magnetic source 206). To further improve the measurement accuracy of the magnetic sensor array 204, the measurements of the array 204 may be verified as discussed in detail below in regard to process step 502 of algorithm 500 shown in FIG. 11.

It should be appreciated that the magnetic sensor arrangement 252 is only one illustrative embodiment and that, in other embodiments, the sensor arrangement 252 of the sensor circuit 250 may include any number of magnetic sensors 350 positioned in any configuration that allows the magnetic sensors 350 to measure the three-dimensional X-, Y-, and Z-components of the measured magnetic flux density. For example, in some embodiments, the magnetic sensor arrangement 252 may include a single three-dimensional magnetic sensor. Alternatively, in other embodiments, the magnetic sensor arrangement 252 may include additional magnetic sensors 350 arranged in various configurations. It should be appreciated that by increasing the number of magnetic sensors, an amount of redundancy is developed. That is, magnitudes of the individual components of the measured magnetic flux densities are determined using measurements from a number of magnetic sensors 350 positioned in different locations. For example, referring to the illustrative magnetic sensor arrangement 252 illustrated in FIG. 9, the magnitudes of the Z-component of the measured magnetic flux densities are determined using the measurements from magnetic sensors $350_1$-$350_{13}$. As such, it should be appreciated that the accuracy of the characterization of the three-dimensional magnetic field generated by the magnetic source 206 may be increased by including additional magnetic sensors in the magnetic sensor arrangement 252.

Further, although the magnetic sensors 350 are embodied as separate magnetic sensors apart from the processing circuit 352 in the illustrative embodiment of FIGS. 7-9, in some embodiments, the magnetic sensors 350 and the processing circuit 352, or portions thereof, may be embodied as a single electronic device. For example, the magnetic sensors 350 and portions of the processing circuit 352 may be embodied as one or more complimentary metal oxide semiconductor (CMOS) device(s). By embedding the magnetic sensors 350 and processing circuit 352 in a semiconductor device, the required space of the sensor circuit 250 is reduced. Additionally, such a semiconductor device may be less susceptible to outside influences such as temperature variation of the individual magnetic sensors 350.

Referring back to FIG. 8, the processing circuit 352 may be embodied as any collection of electrical devices and circuits configured to determine the position of the magnetic source 206. For example, the processing circuit 352 may include any number of processors, microcontrollers, digital signal processors, and/or other electronic devices and circuits. In addition, the processing circuit 352 may include one or more memory devices for storing software/firmware code, data values, and algorithms.

In some embodiments, the processing circuit 352 is configured to determine position data indicative of the position of the magnetic source 206 relative to the magnetic sensor array 204 based on the measurements of magnetic sensors 350. To do so, the processing circuit 352 may execute an algorithm for determining the position of the magnetic source 206 relative to the magnetic sensor array 204 as discussed in detail below in regard to algorithms 600 and 650 and illustrated in FIG. 13 and 14. The position data may be embodied as coefficient values or other data usable by the controller 208, along with pre-operative images of the relevant bones and magnetic sources 206, to determine the position (i.e., location and orientation) of the magnetic source 206. The processing circuit 352 controls the transmitter 354 via interconnect 358 to transmit the position data to the controller 208 via the communication link 234. Alternatively, in other embodiments, the processing circuit 332 is configured only to transmit the measurements of the magnetic sensors 350 to the controller 208 via the transmitter 354. In response, the controller 208 executes the algorithm for determining the position of the magnetic source 206 using the measurements received from the magnetic sensor array 204. In such embodiments, the overall footprint (i.e., size) of the sensor circuit 250 may be reduced because some of the circuitry of the processing circuit 352 may not be required since the processing circuit 352 is not configured to determine the position data.

In some embodiments, the sensor circuit 250 may also include an indicator 360. The indicator 360 may be embodied as any type of indicator including a visual indicator, an audible indicator, and/or a tactile indicator. The indicator 360 is electrically coupled to the processing circuit 352 via an interconnect 362, which may be similar to interconnects 356, 358. In such embodiments, the processing circuit 352 is configured to activate the indicator 360 when the magnetic sensor array 204 (i.e., the magnetic sensors 350) is positioned in a magnetic field of a magnetic source 206. For example, the processing circuit 352 may be configured to monitor the magnetic flux densities sensed by the magnetic sensor(s) 350 in one or more of the X-, Y-, and/or Z-directions shown in FIG. 9 and activate the indicator 360 when the magnetic flux density in one or more of the X-, Y-, and/or Z-directions reaches or surpasses a predetermined threshold value. In this way, the magnetic sensor array 204 is capable of notifying the surgeon 50 or other user of the array 204 when the array 204 has been properly positioned such that the magnetic sensor array 204 can accurately sense or measure the magnetic flux density of the magnetic source 206.

Further, in some embodiments the sensor circuit 250 may include a register button 364. The register button 364 may be located on an outside surface of the magnetic sensor array 204 such that the button 364 is selectable by a user (e.g., an orthopaedic surgeon 50) of the array 204. The button 364 may be embodied as any type of button such as a push button, toggle switch, software implemented touch screen button, or the like. The register button 364 is electrically coupled to the processing circuit 352 via an interconnect 366, which may be similar to interconnects 356, 358. The register button 364 may be selected by a user, such as an orthopaedic surgeon, of the magnetic sensor array 204 to transmit the position data and/or measurement values of the magnetic sensors 350 to the controller 208. That is, as discussed in more detail below in regard to algorithm 600, once the magnetic sensor array 204 is properly positioned to measure the magnetic field of the magnetic source 206, the surgeon 50 may select the register button 364 to cause the magnetic sensor array 204 to transmit the data. In some embodiments, the register button 364 is only operable while the magnetic 204 is properly positioned. For example, the register button 364 may be selected to transmit the position data/measured values only while the processing circuit 352 has determined that the measured magnetic flux density (e.g., in the Z-axis direction) is above a predetermined threshold value or within a predetermined range of values. As discussed above in regard to the indicator 360, the surgeon 50 is notified when the magnetic sensor array is properly positioned by the activation of the indicator 360.

Although the illustrative magnetic sensor array 204 is illustrated as a hand-held device including the sensor circuit 250 located therein, in other embodiments, the magnetic sensor array 204 may be embodied as a single magnetic sensor, a number of magnetic sensors, or a collection of magnetic sensors and other circuitry. Additionally, in other embodiments, the magnetic sensor array 204 may include one or more remote magnetic sensors located apart from the sensor circuit 250. By displacing the remote magnetic sensor(s) from the sensor circuit 250, unwanted magnetic interferences caused by environmental magnetic fields such as magnetic effects caused from the Earth's magnetic field, stray magnetic fields in the operating room, and the like, may be adjusted out of or otherwise compensated for in the sensor circuit 250 as discussed in more detail below in regard to process step 652 of algorithm 650 described below in regard to and illustrated in FIG. 14.

Figure 10:
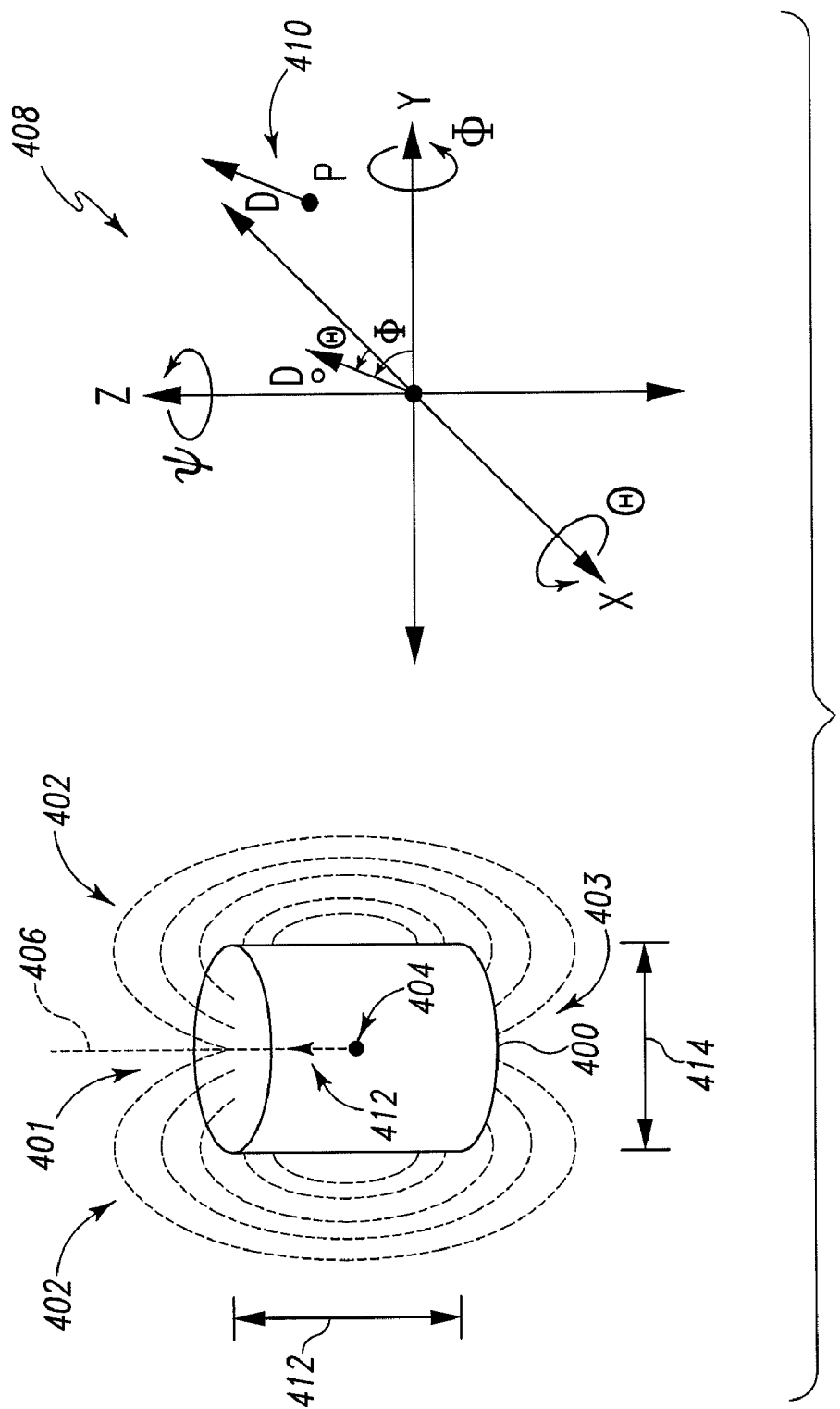
FIG. 10 is a perspective view of one embodiment of a magnetic source.

Referring now to FIG. 10, the magnetic source 206 may be embodied as one or more magnets. In the illustrative embodiment, the magnetic source 206 is embodied as two or more cylindrical, dipole magnets 400. The magnet(s) 400 generate a magnetic field having a number a magnetic flux lines 402. It should be appreciated that only a subset cross-section of the generated flux lines 402 is illustrated in FIG. 10 and that the flux lines (and magnetic field) circumferentially surround the magnet(s) 400. Each of the magnets 400 includes a centroid 404 (illustrated in FIG. 10 as a dot) and an axis 406. Additionally, each magnet 400 includes a north pole 401 and a south pole 403, through which the axis 406 is defined. When coupled to a bone(s) of a patient, the position (i.e., location and orientation) of the magnets 400 is defined by six degrees of freedom. That is, the position of the magnet(s) 400 can be defined by three Cartesian coordinate values and three rotational values (i.e., one about each Cartesian axis). For example, as illustrated in FIG. 10 by coordinate system 408, the position of the magnet(s) 400 can be defined in three-dimensional space by an X-coordinate value, a Y-coordinate value, a Z-coordinate value, a (theta) θ-rotational value about the X axis, a (phi) φ-rotational value about the Y axis, and a (psi) Ψ-rotational value about the Z axis.

The position (i.e., location and orientation) of the magnets 400 may alternatively be defined with six degrees of freedom in the coordinate system 408 as a point coordinate (P) and direction vector (D) based on the centroid 404 and a vector 412 originating at the centroid 404 and extending along the axis 406. The vector 412 may be defined to point in any one of the polar directions and is illustrated in FIG. 10 as pointing toward the north pole of the magnet 400. The point coordinate (P) correlates to the location of the centroid 404 of the magnet 400 in the coordinate system 408 and may be defined by an X-coordinate value, a Y-coordinate value, and a Z-coordinate value. The direction vector (D) correlates to the vector 12 of the magnet 400 in the coordinate system 408. The direction vector (D) may also be defined as a unit vector (Do) as follows:

$$D_o = \frac{ai + bj + ck}{\sqrt{a^2 + b^2 + c^2}}$$

wherein i is a unit vector pointing in the X direction, j is a unit vector pointing in the Y direction, k is a unit vector pointing in the Z direction, and a, b, and c are numerical values. Additionally or alternatively, the position of the magnets 400 may be defined with six degrees of freedom as the point coordinate (P) discussed above and two angular values defining the direction of the direction vector (D). For example, as illustrated in FIG. 10, the direction vector (D) may be defined as a (theta) θ-rotational value about the X axis and a (phi) φ-rotational value about the Y axis. In such embodiments, the values theta and phi may be determined based as follows:

θ=arctangent (b/a)
φ=arccosine (c)

The magnet 400 may be formed from any magnetic material capable of generating a magnetic field of sufficient magnetic flux density or strength to be sensed or measured by the sensor circuit 250 through the relevant tissue of a patient. For example, the magnet 400 may be formed from ferromagnetic, ferrimagnetic, antiferromagnetic, antiferrimagnetic, paramagnetic, or superparamagnetic material. In one particular embodiment, the magnet 400 is formed from a neodymium iron boron (NdFeB) grade 50 alloy material. The illustrative magnet 400 is a cylindrical magnet having a length 412 of about five millimeters and a diameter 414 of about two millimeters. However, in other embodiments, magnets 400 having other configurations, such as rectangular and spherical magnets, and sizes may be used.

To improve the accuracy of the measurements of the magnetic sensors 350, in some embodiments, the plurality of magnets 400 that embody the magnetic source 206 are formed or manufactured such that the magnetic qualities of each magnet 400 are similar. To do so, in one embodiment, the magnetic field generated by each magnet 400 is measured and determined. Only those magnets 400 having similar magnetic fields are used. Additionally, in some embodiments, the magnetic moment of each magnet 400 may be determined. Only those magnets 400 with magnetic moments on-axis or near on-axis with the magnet's 400 longitudinal axis are used. That is, if the magnetic moment of the magnet 400 is determined to extend from the magnet 400 from a location substantially off the longitudinal axis of the magnet 400, the magnet 400 may be discarded. In this way, the magnetic fields generated by each of the magnets 400 are similar and, as such, measurements of the magnetic fields and calculated values based thereon may have increased accuracy.

Referring now to FIGS. 11-20, an algorithm 500 for registering a bone of a patient with a computer assisted orthopaedic surgery (CAOS) system (e.g., the CAOS system 202) begins with an optional process step 502 in which the accuracy of the magnetic sensor array 204 is verified (e.g., the accuracy of the measurements of the magnetic sensors 350 may be verified). Such verification process may be executed before each registration procedure or as part of a maintenance routine such as a yearly, monthly, or weekly maintenance procedure. For example, in some embodiments, a gage repeatability and reproducibility process may be used to ensure that the magnetic sensor array 204 functions properly across a number of different users and uses. In one particularly embodiment, a test apparatus may be coupled to the sensing head portion 236 of the magnetic sensor array 204 to verify the accuracy of the magnetic sensor array 204.

An exemplary test apparatus includes a test magnetic source positioned at a predetermined distance from the sensor circuit 250 housed in the sensing head portion 236 of the magnetic sensor array 204. Because the magnetic flux density (or magnetic strength) of the test magnetic source is known and the distance of the test magnetic source from the sensing head portion 236 is known (i.e., from the sensor circuit 250 located in the sensing head 236), an expected magnetic flux density measurement value for each magnetic sensor 350 can be determined. The actual measured magnetic field values of each magnetic field sensor 350 (i.e., the output voltage levels of the magnetic sensors 350 indicative of one or more axes of the three-dimensional magnetic flux density components at each sensor's position) may then be compared to the expected magnetic flux density values. Any error above a predetermined threshold may be indicative of malfunction of the magnetic sensor array 204. To further improve the verification procedure, the test apparatus may be selectively positioned in a number of locations from the sensing head 236. Expected and measured magnetic flux density values may then be determined for each such location.

Next, in process step 504, the magnetic source 206 is coupled to the relevant bony anatomy of the patient. The magnetic source 206 may be implanted in or otherwise fixed to the bone or bones of the patient upon which the orthopaedic surgical procedure is to be performed. For example, if a total knee arthroplasty (TKA) surgical procedure is to be performed, one or more magnetic sources 206 may be coupled to the relevant tibia bone, the relevant femur bone, or both the relevant tibia and femur bones of the patient. As discussed above, each magnetic source 206 may be embodied as one or more magnets 400.

Figure 16:
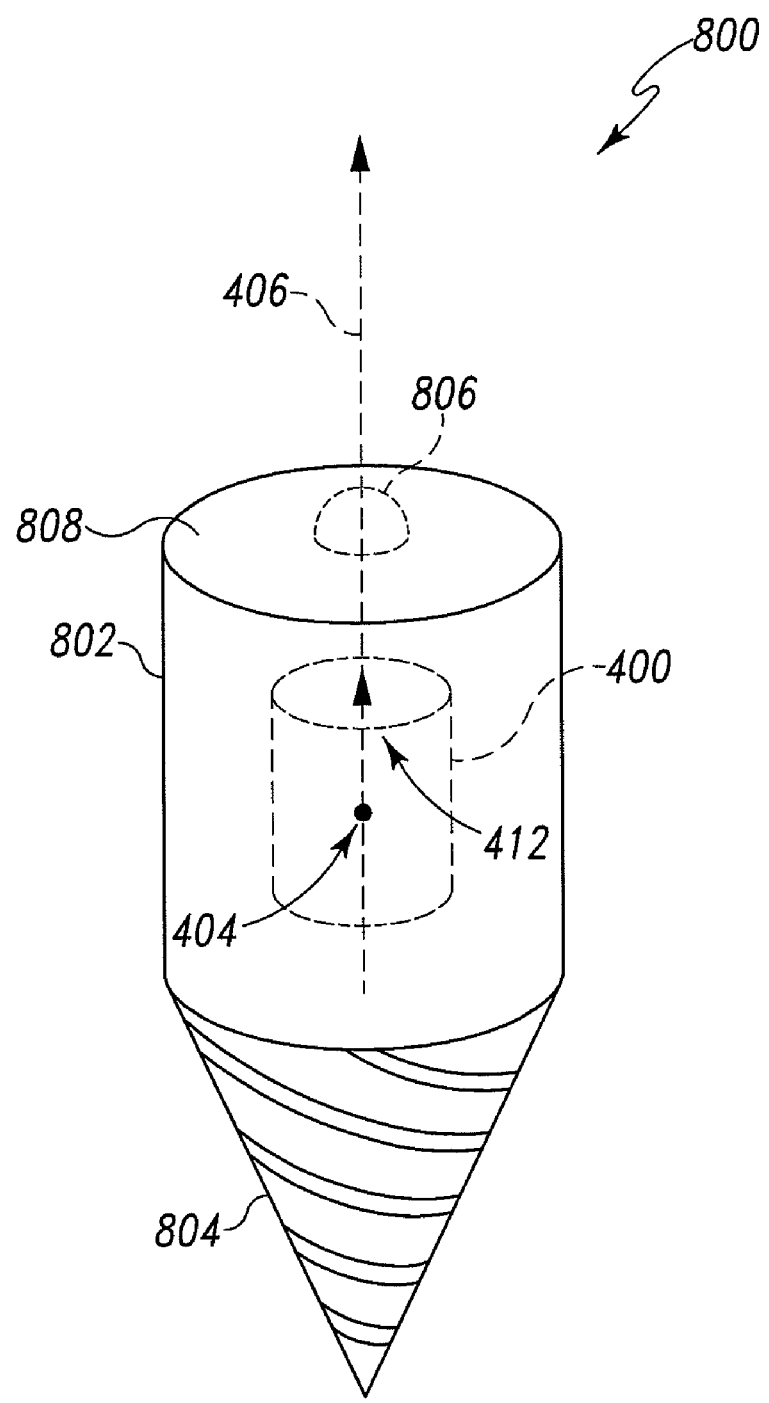
FIG. 16 is a perspective view of an implantable capsule for use with the magnetic source of FIG. 10.

The magnet(s) 400 that embody the magnetic source 206 may be coupled to the bone of the patient using any suitable fixation means that secures the magnet(s) 400 to the bone such that the magnet(s) 400 do not move or otherwise propagate about before and during the performance of the orthopaedic surgical procedure. In one embodiment, the magnet(s) 400 are coupled to the bone of the patient by implanting the magnet(s) 400 in the bone. To do so, as illustrated in FIG. 16, an implantable capsule 800 may be used. The capsule 800 includes a body portion 802 in which a magnet 400 is located and a threaded screw portion 804 at a distal end of the body portion 802. The capsule 800 may be formed from any non-magnetic material, such as a ceramic or plastic material, such that the magnetic field generated by the magnet 400 is not degraded by the capsule 800. Additionally, the capsule 800 is formed from a radioopaque material (e.g., a radioopaque ceramic) such that the capsule 800 is distinguishable in a medical image of the bone (e.g., in a Computed Tomography (CT) image, X-Ray image, or the like). The capsule 800 (and the magnet 400) may be implanted in a bone of the patient by first boring a suitable hole into the bone and subsequently inserting the capsule 800 by, for example, screwing the capsule 800, into the bored hole. In other embodiments, implantable capsules having other configurations may be used. For example, in some embodiments, the implantable capsule may include threads that cover the entire body of the capsule.

As discussed above in regard to FIG. 10, the position of the magnet 400 once coupled to the bone of the patient may be defined by a location of the centroid 404 of the magnet 400 and the direction of one of the polar axis of the magnet 400. In embodiments wherein the implantable capsule 800 is used, the capsule 800 may include indicia from which the direction of the polar axis 406 of the magnet 400 may be determined in a medical image when the magnet 400 is positioned in the body portion 802. For example, in some embodiments, the direction of the polar axis 406 may be determined based on the direction of the screw portion 804, which is visibly distinguishable in a medical image when the capsule 800 is formed from a radioopaque material. Alternatively or additionally, the capsule 800 may include a direction indicator 806 on a top surface 808 of the capsule 800, such as protrusion or the like, which provides additional indication of the direction of the polar axis 406 of the magnet 400. In such embodiments, the magnet 400 may be positioned in the capsule 800 is a predetermined orientation. For example, the magnet 400 may be positioned in the capsule 800 such that the north polar axis extends through the top surface 808 of the capsule 800. In this way, the direction of each polar axis of a number of magnets 400, which may embody the magnetic source 206 in some embodiments, may be determined.

In embodiments wherein the magnetic source 206 is embodied as a number of magnets 400, the magnets 400 may be coupled or implanted into the bone of the patient at a predetermined, known position (location and/or rotation) relative to each other. For example, the two magnets 400 may be implanted into the bone of the patient such that the magnets 400 are substantially orthogonal to each other or otherwise implanted with a known angle defined between each other. Regardless, the magnets 400 are implanted a distance apart from each other such that the magnetic fields generated by the magnets 400 do not interfere with each other. That is, the magnets 400 are separated by a sufficient distance such that the magnetic field of one magnet 400 does not constructively or destructively interfere with the magnetic field of another magnet 400 over the intended measurement region. In one particular embodiment, the magnets 400 are implanted a distance of two times or more the maximum desired measuring distance (e.g., the maximum Z-axis distance from the magnets 400 that the magnetic sensor array 204 can be positioned while still accurately measuring the magnetic field of the magnets 400).

In some embodiments, a jig or guide may be used to facilitate the implanting of two or more magnets 400 at a predetermined distance from each other (and predetermined angles of rotation relative to each other if so desired). In other embodiments, the two or more magnets 400 that form the magnetic source 206 may be secured to each other via a fixed brace or support member. The support member secures the magnets 400 at a predetermined three-dimensional position (i.e., location and orientation) with respect to each other. In such embodiments, a jig may not be required to implant the magnets 400. However, because the support member may form a magnetic source 206 that is structurally larger, a larger incision may be required to implant the magnetic source 206 into the bone of the patient.

In embodiments wherein the magnetic source 206 is formed from two or more magnets 400, the magnetic sensor array 204 may be used by positioning the array 204 (i.e., the sensor circuit 250) in the magnetic field of the one of the magnets 400, sensing the magnetic field of the that magnet 400 to determine position data indicative of its position relative to the magnetic sensor array 204, and then positioning the magnetic sensor array 204 in the magnetic field of the next magnet 400 relative to the magnetic sensor array 204, sensing the magnetic field of the next magnet 400, and so on.

Figure 11:
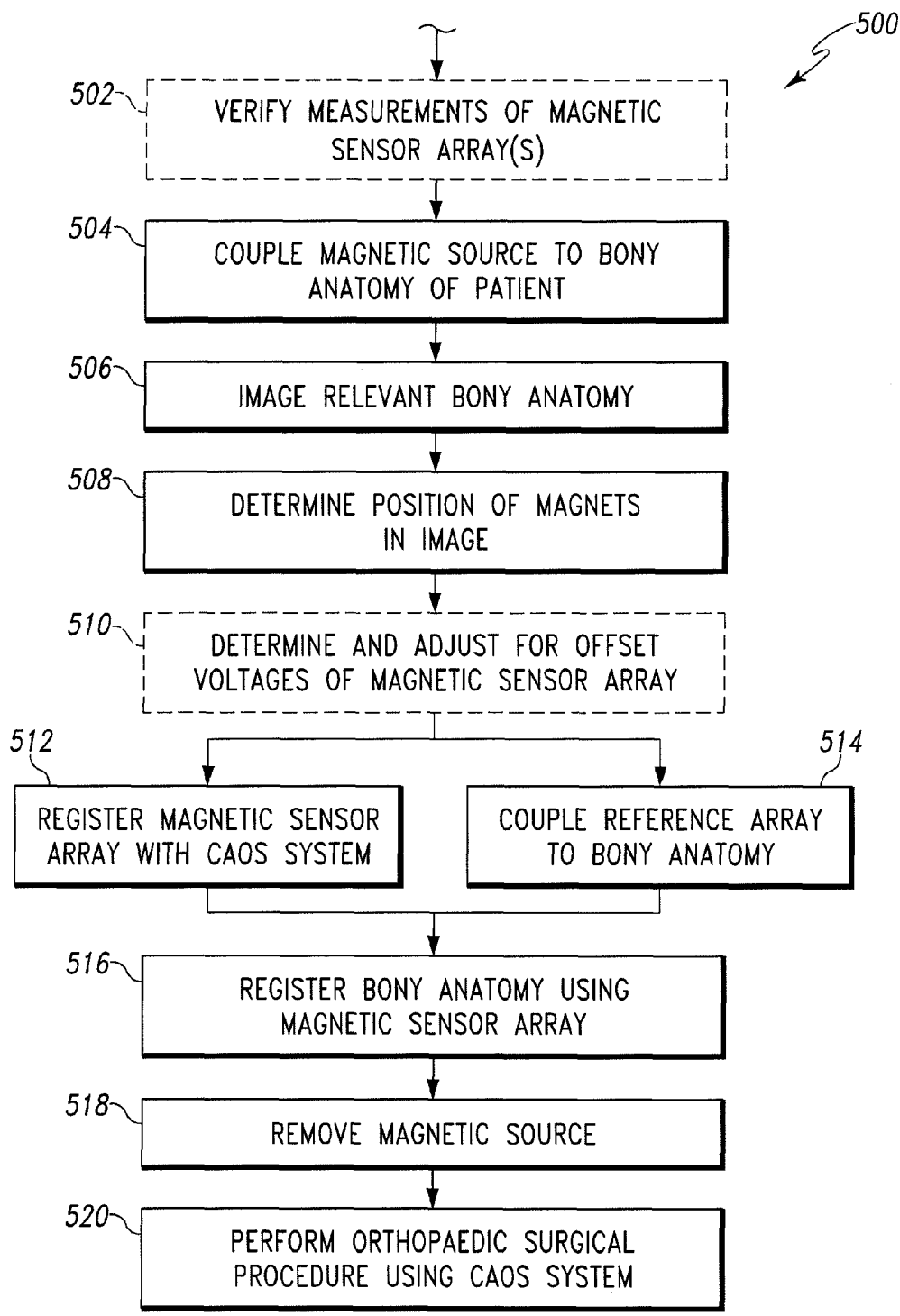
FIG. 11 is a simplified flowchart of an algorithm for registering a bone of a patient with a computer assisted orthopaedic surgery system.

Referring now back to FIG. 11, after the magnetic source 206 has been coupled to the bone of the patient in process step 504, an image of the bone or bones having the magnetic source 206 coupled thereto is generated in process step 506. It should be appreciated that the magnetic source 206 is coupled to the bone of the patient prior to the performance of the orthopaedic surgical procedure. As such, the magnetic source 206 may be coupled to the bone of the patient well in advance of the date or time of the orthopaedic surgical procedure or immediately preceding the procedure. Accordingly, the image of the bone or bony anatomy of the patient may be generated any time after the coupling step of process step 504. For example, the bone(s) of the patient may be imaged immediately following process step 504, at some time after the completion of process step 504, or near or immediately preceding the performance of the orthopaedic surgical procedure.

The relevant bone(s) of the patient (i.e., the bone(s) which have the magnetic source 206 coupled thereto) may be imaged using any suitable bony anatomy imaging process. The image so generated may be a number of two-dimensional images or three-dimensional images of the relevant bone(s) of the patient and includes indicia of the position of the magnetic source 206 coupled to the bone(s). That is, the image is generated such that the position (i.e., location and orientation) of the magnets 400 implanted or otherwise fixed to the relevant bone(s) is visible and/or determinable from the image. To do so, any image methodology capable of or usable to generate a three-dimensional image of the relevant bone(s) and magnetic source 206 may be used. For example, computed tomography (CT), fluoroscopy, and/or X-ray may be used to image the bone.

Figure 12:
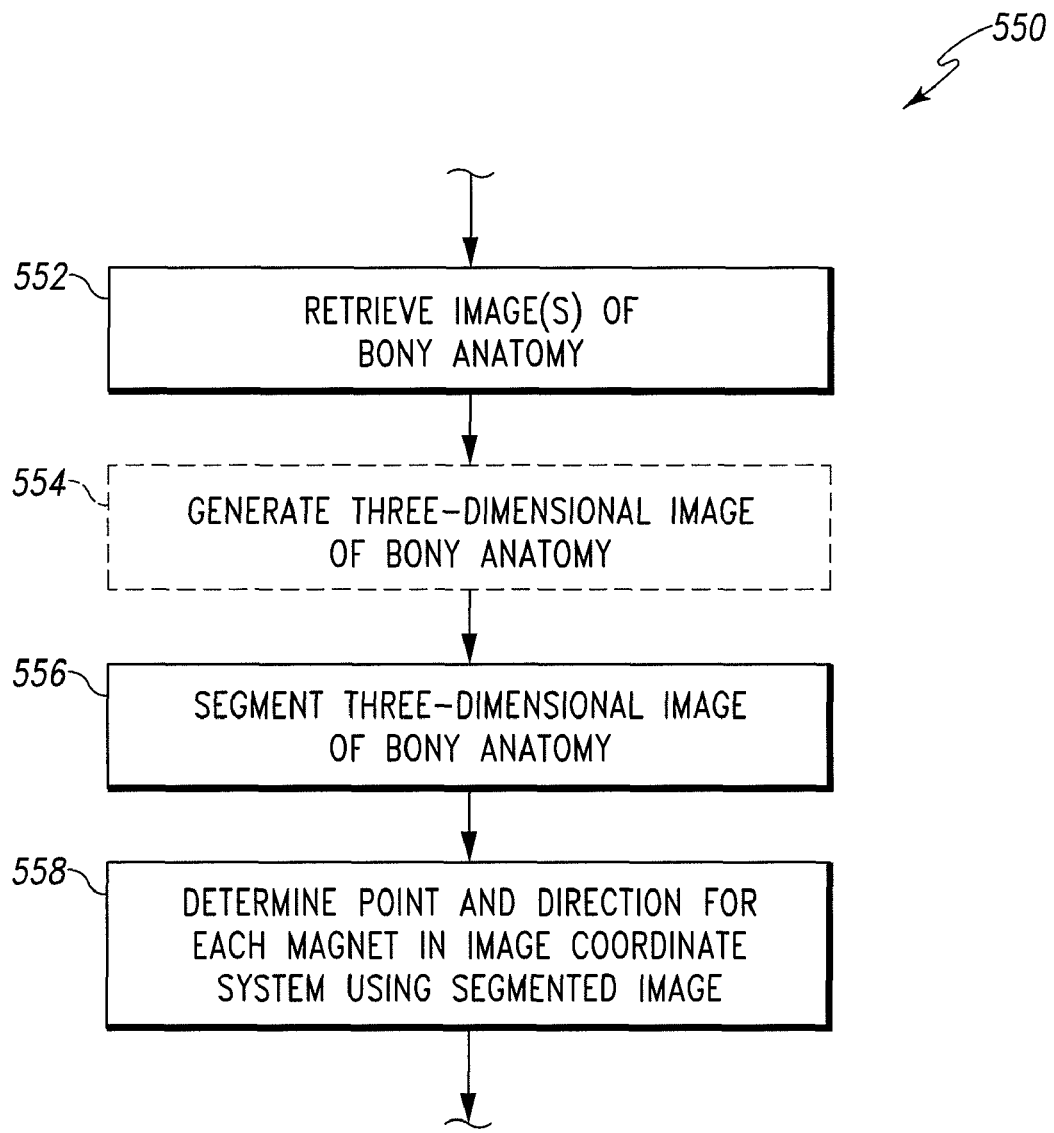
FIG. 12 is a simplified flowchart of an algorithm for determining a position of a magnet in an image.

Subsequently, in process step 508, the position (i.e., the location of the centroid and direction of the polar axis) of each magnet 400 in the image is determined. To do so, the computer assisted orthopaedic surgery system 202 may execute an algorithm 550 for determining the position of each magnet 400 in the image as illustrated in FIG. 12. The algorithm 550 begins with a process step 552 in which the image(s) of the bony anatomy is retrieved. The controller 208 may retrieve the image(s) from the memory device 224, the database 226, the remote database 228, or other storage location. Alternatively, the image(s) may be supplied to the computer assisted orthopaedic surgery system 202 on a portable media device such as a compact disk, portable memory device, or the like. Any number of images may be retrieved in process step 552. For example, in embodiments wherein the images are embodied as two-dimensional images (e.g., two-dimensional X-ray images), the computer assisted orthopaedic surgery system 202 may retrieve two or more such images.

Additionally, in embodiments wherein the images are embodied as a number of two-dimensional images, a three-dimensional image is generated from the two-dimensional images in process step 554. For example, in some embodiments, two non-coplanar X-ray images may be used to form a three-dimensional image of the relevant bone(s) and magnetic source 206. For example, the two or more non-coplanar X-ray images may be generated in process step 506 of algorithm 500 and subsequently compared with each other to determine the three-dimensional image. To do so, any two-dimensional-to-three-dimensional morphing algorithm may be used. For example, any one or combination of the morphing algorithms disclosed in U.S. Pat. Nos. 4,791,934, 5,389,101, 6,701,174, U.S. Patent Application Publication No. US2005/0027492, U.S. Patent Application Publication No. US2005/0015003A1, U.S. Patent Application Publication No. US2004/0215071, PCT Patent No. WO99/59106, European Patent No. EP1348394A1, and/or European Patent No. EP1498851A1 may be used.

Once a three-dimensional image of the relevant bony anatomy and magnetic source 206 has been generated, the algorithm 550 advances to process step 556. In process step 556, the three-dimensional image is segmented to distinguish the indicia of the magnetic source 206 (i.e., magnets 400) from the remaining background of the image. Any type of segmentation algorithm may be used. For example, a threshold-based algorithm, an edge-based algorithm, a region-based algorithm, or a connectivity-preserving relaxation-based algorithm may be used. In one particular embodiment, a threshold-based algorithm is used to filter the three-dimensional image such that indicia having an intensity value lower than a predetermined minimum threshold is removed from the image. For example, the segmentation algorithm may analyze each voxel forming the three-dimensional image and "turn off" (i.e., set to a value of 0) each voxel having an intensity value less than the predetermined minimum threshold value. Because the magnet 400 (and capsule 800 in some embodiments) is radioopaque, the voxels forming the image of the magnet 400 (and capsule 800) will remain in the image such that the magnet 400 and/or capsule 800 is discernable in the image.

Figure 17:
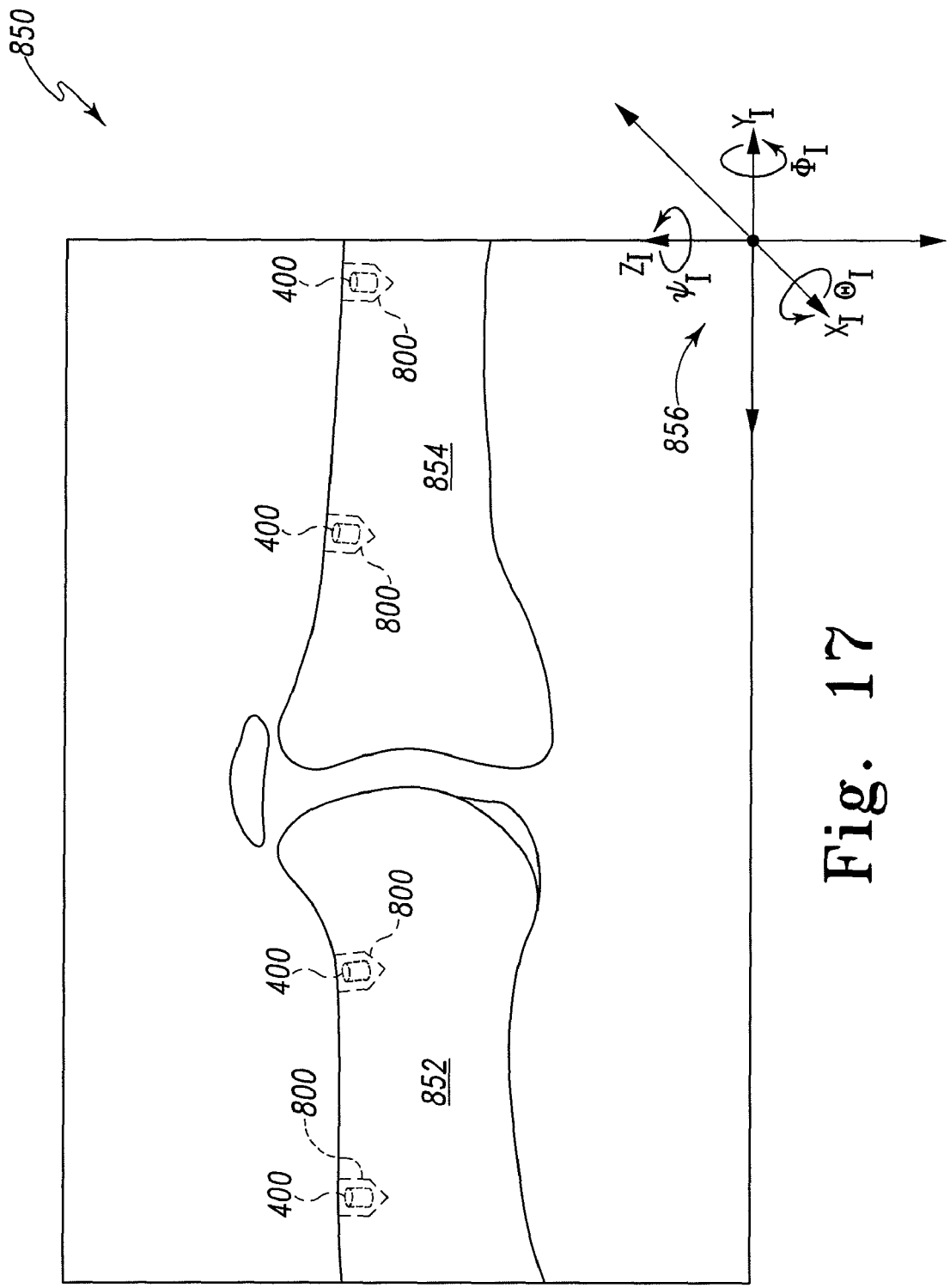
FIG. 17 is an illustration of a three-dimensional image of a patient's bony anatomy having a magnetic source coupled thereto.

For example, as illustrated in FIG. 17, a three-dimensional image 850 of a knee joint of a patient may include indicia of the femur 852 and tibia 854 of the patient. A magnetic source 206 is implanted in the femur 852 and tibia 854. The illustrative magnetic source 206 is embodied as four magnets 400 positioned in capsules 800 and individually coupled to the femur 852 or tibia 854. An image coordinate system 856 may be defined in the image 850 such that positions of indicia in the image (e.g., the magnets 400) may be referenced to the coordinate system 856. In the illustrative embodiment of FIG. 17, the coordinate system 856 is defined as having an origin at the bottom right corner of the image 850. However, in other embodiments, the origin of the coordinate system 856 may be defined at any other corner of the image 850 or at any location within the image 850.

Figure 18:
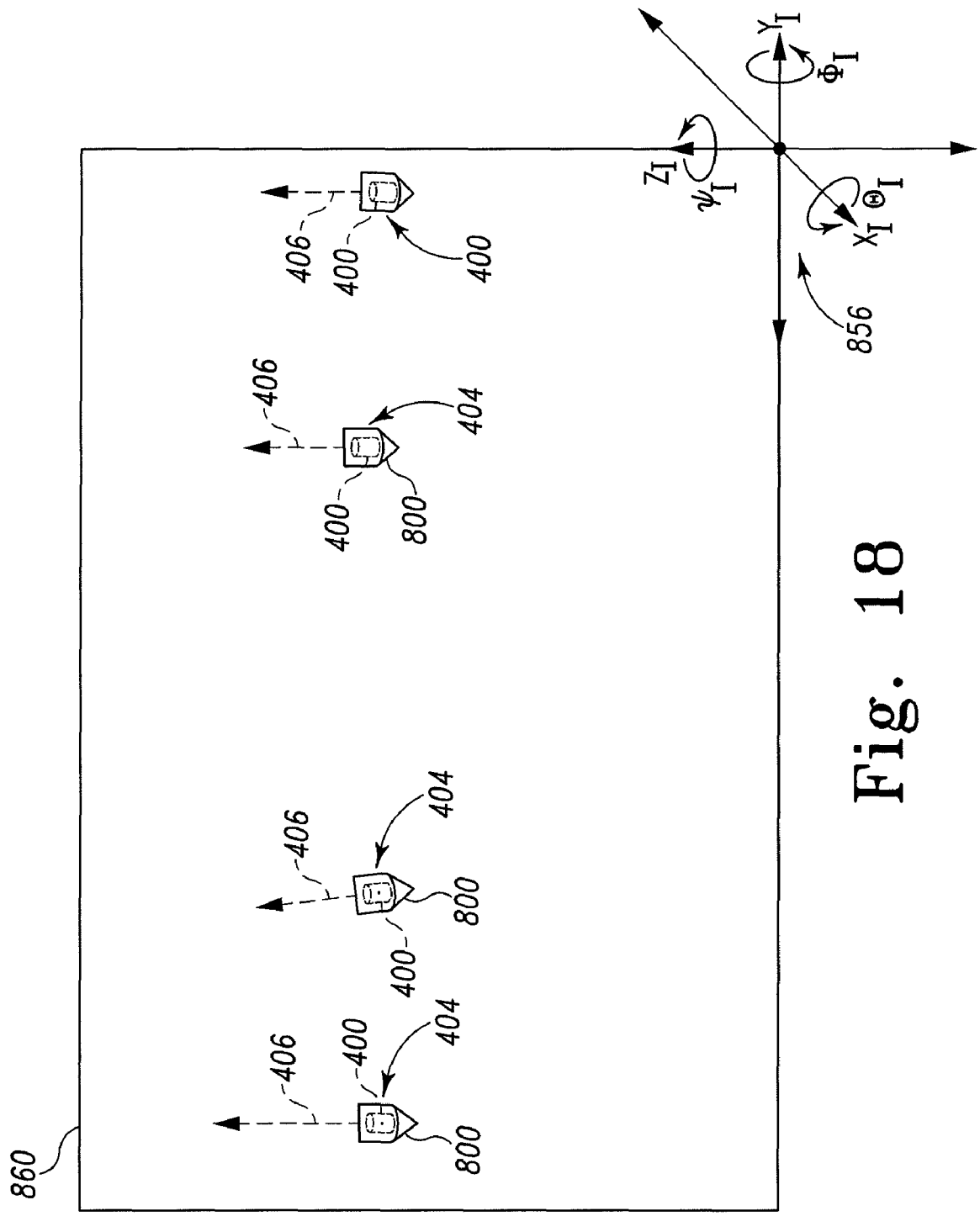
FIG. 18 is an illustration of the image of FIG. 18 after a segmentation process has been applied to the image.

As illustrated in FIG. 18, a segmented image 860 is generated by segmenting the three-dimensional image 850. After the segmentation process, the implantable capsules and/or magnets 400 are more easily discernable from the other indicia of the image 850, such as the femur 852 and tibia 854. In particular, depending on the segmentation process, the segmented image 860 may include only indicia of the magnets 400 and/or capsules 800 as illustrated in FIG. 18.

Once the image has been segmented, the position of the each magnet 400 is determined in process step 558. To do so, the location of the centroid 404 and the vector 412 along the axis 406 of each magnet 400 is determined from the segmented image 860. The centroid 404 of the magnets 400 may be determined by locating the center of the volume of voxels that form the image of each magnet 400 (or capsule 800) in the segmented image 860. The vector 412 may be determined by locating the longitudinal axis of the volume of voxels forming each magnet 400 and/or based on the direction of other indicia such as the indicator 806 of the implantable capsule 800. The location, $P_I$, of the centroid 404 of each magnet 400 may be represented by a three-dimensional coordinate value (X, Y, Z) with respect to the image coordinate system 856. Similarly, the direction vector, $D_I$, defined along the axis 406 of each magnet 400 may be defined as a unit vector with respect to the image coordinate system 856 as follows:

$$D_I = \frac{ai + bj + ck}{\sqrt{a^2 + b^2 + c^2}}$$

wherein i is a unit vector pointing in the X direction, j is a unit vector pointing in the Y direction, k is a unit vector pointing in the Z direction, and a, b, and c are numerical values.

In some embodiments, the controller 208 stores the coordinates location, $P_I$, of the centroid 404 and the direction vector, $D_I$, of the axis 406 of each magnet 400 once such values are determined. The controller 208 may store the location and direction data in the memory device 224, the database 226, and/or the remote database 228.

Referring back to FIG. 11, once the position of each magnet 400 in the three-dimensional image 850, 860 has been determined in process step 508, errors due to the magnetic sensors 350 themselves may be determined and compensated for in process step 510. Due to manufacturing tolerances, aging, damage, use, and other factors, the magnetic sensors 350 may generate an offset output signal (i.e., offset voltage) in the absence of a magnetic field. If the offset output signal of the magnetic sensors 350 is known, the accuracy of the magnetic sensor 308 can be improved by subtracting the offset of the magnetic sensors 350 from the measurements of the magnetic sensors 350. To do so, the magnetic sensor array 204 may be positioned in a magnetically shielded case or housing. The magnetically shielded case is configured to block a significant amount of outside magnetic fields such that the environment contained inside the case is substantially devoid of any magnetic fields. In one embodiment, the magnetically shielded case is formed from a mu-metal material such as particular nickel alloys or from other materials having suitable shielding properties.

To compensate for the offset voltage of the magnetic sensors 350, the magnetic sensor array 204 may be positioned in the magnetically shielded case and operated remotely, or autonomously via an error compensation software program, to measure the output signals of the magnetic sensors 350. Because there is no significant magnetic field inside the magnetically shielded case, the output signals of the magnetic sensors 350 are indicative of any offset voltage errors. Once the offset voltage errors are so determined, the accuracy of the magnetic sensor array 204 may be improved. That is, the sensor circuit 250 may be configured to subtract such offset voltages from the measurements of the magnetic sensors 350 to thereby account for the offset errors. It should be appreciated that the process step 510 may be performed any time prior to the performance of the registration of the bone or bony anatomy (see process step 516 below). In one particular embodiment, the process step 510 is executed just prior to the registration of the relevant bone(s) such that the reduced time lapse between the process step 510 and the registration process reduces the likelihood that the errors drift or change.

Subsequently, the magnetic sensor array 204 is registered with the controller 208 in process step 512 and a reference array is coupled to the relevant bony anatomy in process step 514. As shown in FIG. 11, the process steps 512, 514 may be executed contemporaneously with each other or in any order. Unlike process steps 504-508, the process step 512 is typically performed immediately prior to the performance of the orthopaedic surgical procedure. To register the magnetic sensor array 204, the array 204 is positioned in the field of view 52 of the camera unit 210 such that the reflective reference array 244 is viewable by the camera unit 210. Appropriate commands are given to the controller 208 such that the controller 208 identifies the magnetic sensor array 204 via the reflective reference array 244 coupled thereto. The controller 208 is then capable of determining the position of the magnetic sensor array 204 using the reflective reference array 244.

In process step 514, a reference array is coupled to the relevant bone or bones of the patient. The reference array is similar to reference array 54 illustrated in and described above in regard to FIG. 2. Similar to reference array 54, the reference array may be a reflective reference array similar to reflective reference arrays 244 or may be an electromagnetic or radio frequency (RF) sensor array and embodied as, for example, a wireless transmitter. Regardless, the reference array is coupled to the relevant bony anatomy of the patient such that the reference array is within the field of view of the camera unit 210. The controller 208 utilizes the reference array to determine movement of the bony anatomy once the bony anatomy has been registered with the computer assisted orthopaedic surgery (CAOS) system 202 as discussed below in regard to process step 516.

Figure 13:
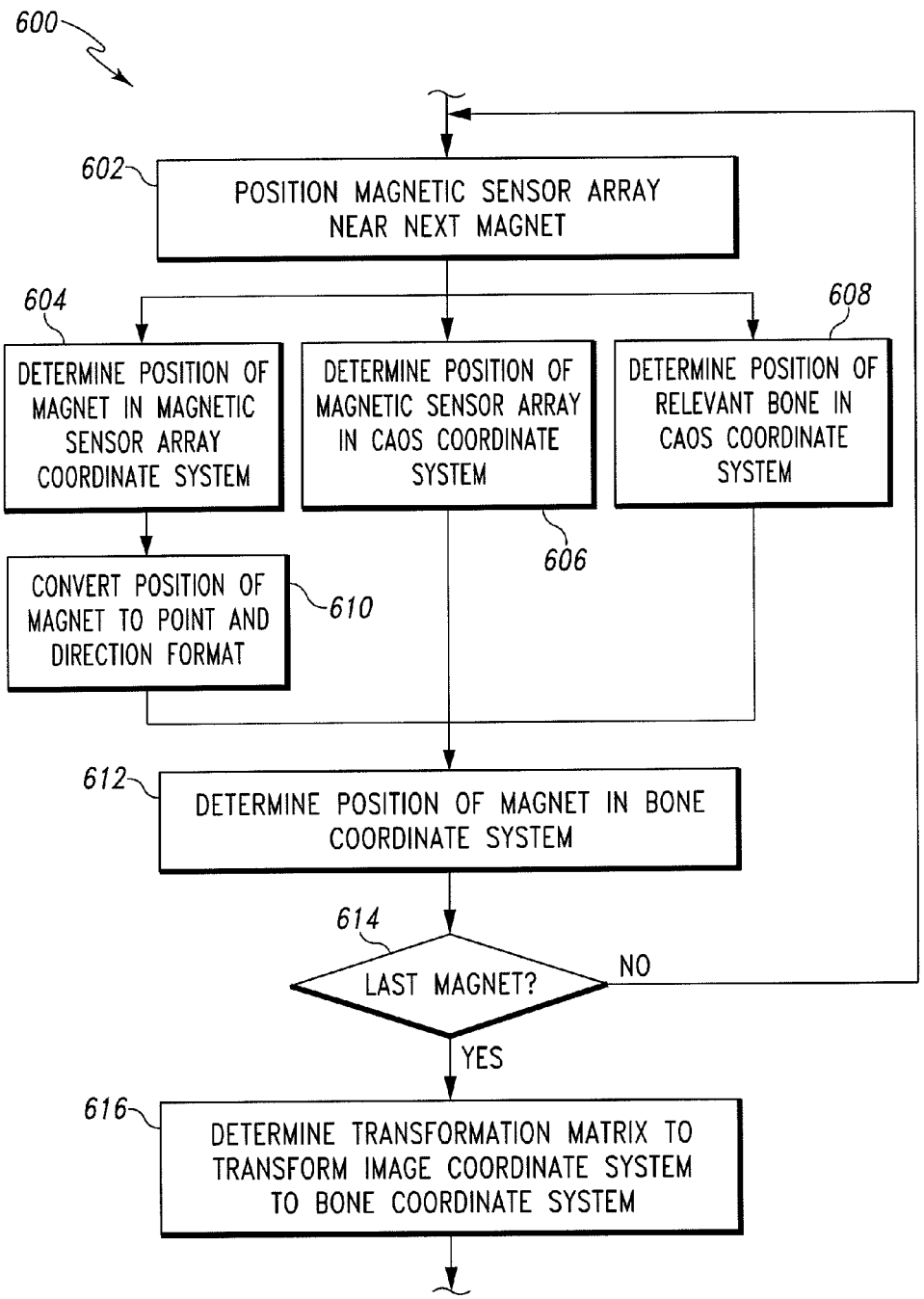
FIG. 13 is a simplified flowchart for transforming the position of a magnet source from a magnet sensor array coordinate system to a bone coordinate system.

After the magnetic sensor array 204 has been registered with the controller 208 in process step 512 and the reference array has been coupled to the relevant bony anatomy in process step 514, the bone or bony anatomy of the patient having the magnetic source 206 coupled thereto is registered with the controller 208 in process step 516. To do so, as illustrated in FIG. 13, an algorithm 600 for transforming the position of a magnetic source from a magnetic sensor array coordinate system to a bone coordinate system may be executed by the controller 208. As will be described below, the algorithm 820 is usable with magnetic sources 206 embodied as any number of magnets 400.

The algorithm 600 begins with process step 602 in which the magnetic sensor array 204 is positioned. To do so, the magnetic sensor array 204 is positioned in the magnetic field of each magnet 400 in a predetermined order based on the three-dimensional image 850, 860. For example, the positioning order of the magnetic sensor array 204 may be distal-to-proximal magnets 400 beginning with the femur of the patient. The magnetic sensor array 204 may be positioned using any order of the magnets 400 such that the position data generated from the magnetic sensor array 204 is associated with the correct magnet 400.

The magnetic sensor array 204 is positioned in the magnetic field of each magnet 400 in process step 602 such that the sensor circuit 250 of the magnetic sensor array 204 is positioned over a magnetic moment of the respective magnet 400. In one particular embodiment, the magnetic sensor array 204 may be positioned such that the central magnetic sensor $350_1$ (see FIG. 9) is substantially on-axis with the magnetic moment of the magnet 400. To do so, the sensor circuit 250 may be configured to monitor the output of the magnetic sensor $350_1$. For example, in the illustrative embodiment, the sensor circuit 250 may be configured to monitor the X-component and the Y-component outputs of the centrally located, three-dimensional magnetic sensor $350_1$. The magnetic sensor array 204 is determined to be positioned over the magnetic moment of the magnet 400 (i.e., the field sensitive point of the magnetic sensor $350_1$ is on-axis or near on-axis with the magnetic moment of the magnet 400) when the measured X-component and Y-component measurements are at a minimum value (or below a threshold value).

In other embodiments, the sensor circuit 250 may be configured to monitor the X-component and the Y-component outputs of additional magnetic sensors 350. For example, the sensor circuit 250 may be configured to monitor the output of all magnetic sensors 350 configured to measure the X-component of the three-dimensional magnetic flux density of the magnet 400 at a given position (e.g., magnetic sensors $350_1$-$350_5$, $350_{15}$, and $350_{17}$) and the output of all the magnetic sensors 350 configured to measure the Y-component of a three-dimensional magnetic flux density of the magnet 400 at a given position (i.e., magnetic sensors $350_1$-$350_5$, $350_{14}$, and $350_{16}$). For example, the sensor circuit 250 may be configured to sum the output of such sensors and determine the location at which such sums are at a minimum value.

To assist the surgeon 50 in positioning the magnetic sensor array 204, the sensor circuit 250 may be configured to provide feedback to the surgeon 50 via the indicator 360. For example, when the sensor circuit 250 determines that the sum of the X-component measurements and the sum of the Y-component measurements have reached minimum values, the sensor circuit 250 may be configured to activate the indicator 360. In this way, the surgeon 50 knows when the magnetic sensor array is properly positioned in the X-Y plane relative to the magnet 400.

In other embodiments, the sensor circuit 250 may be configured to adapt to non-alignment of the magnetic sensor array 204. For example, based on the X-component and Y-component measurement outputs of the magnetic sensors $350_1$-$350_5$ and $350_{14}$-$350_{17}$, the sensor circuit 250 may be configured to determine which magnetic sensor 350 is on-axis or closest to on-axis with the magnetic moment of the magnet 400. For example, if the X-component and Y-component measurement outputs of the magnetic sensor $350_5$ (see FIG. 9) is near zero or at a minimum, the sensor circuit 250 may be determine that the field sensitive point of the magnetic sensor $350_5$ is on-axis or near on-axis with the magnetic moment of the magnet 400. Rather than forcing the surgeon 50 or user to reposition the magnetic sensor 308, the sensor circuit 250 may be configured to adjust measurement values of the magnetic sensors 350 for the X-Y offset of the magnetic moment of the magnet 400 relative to the sensor board 370.

In process step 602, the magnetic sensor array 204 is also positioned along the Z-axis relative to the magnet 400. That is, the magnetic sensor array 204 is positioned a distance away from the magnet 400 along the Z-axis as defined by the magnetic moment of the magnet 400. The magnetic sensor array 204 is positioned at least a minimum distance away from the magnet 400 such that the magnetic sensors 350 do not become saturated. Additionally, the magnetic sensor array 204 is positioned within a maximum distance from the magnet 400 such that the measured magnetic flux density is above the noise floor of the magnetic sensors 350 (i.e., the magnetic flux density if sufficient to be discerned by the magnetic sensors 350 from background magnetic "noise"). The sensor circuit 250 may be configured to monitor the output of the magnetic sensors 350 to determine whether the magnetic sensors 350 are saturated or if the output of the magnetic sensors 350 is below the noise floor of the sensors 350. The sensor circuit 250 may be configured to alert the surgeon 50 or user of the magnetic sensor array 204 if the magnetic sensor array 204 is properly positioned with respect to the Z-axis relative to the magnet 400. The maximum distance at which the magnetic sensor array 204 will be used also determines the minimum distance between the individual magnets 400 that form the magnetic source 206 (i.e., the magnets 400 are separated by a distance of two times or more the maximum measurement distance of the magnetic sensor array 204 in one embodiment).

Once the magnetic sensor array 204 has been properly positioned in process step 602, the position of each magnet 400 relative to the magnetic sensor array 204 is determined in process step 604. Additionally, the position of the magnetic sensor array 204 relative to the computer assisted orthopaedic surgery system 202 is determined in process step 606 and the position of the relevant bone or bony anatomy is determined in process step 608. As illustrated in FIG. 13, the process steps 604, 606, 608 are executed contemporaneously with each other.

Figure 19:
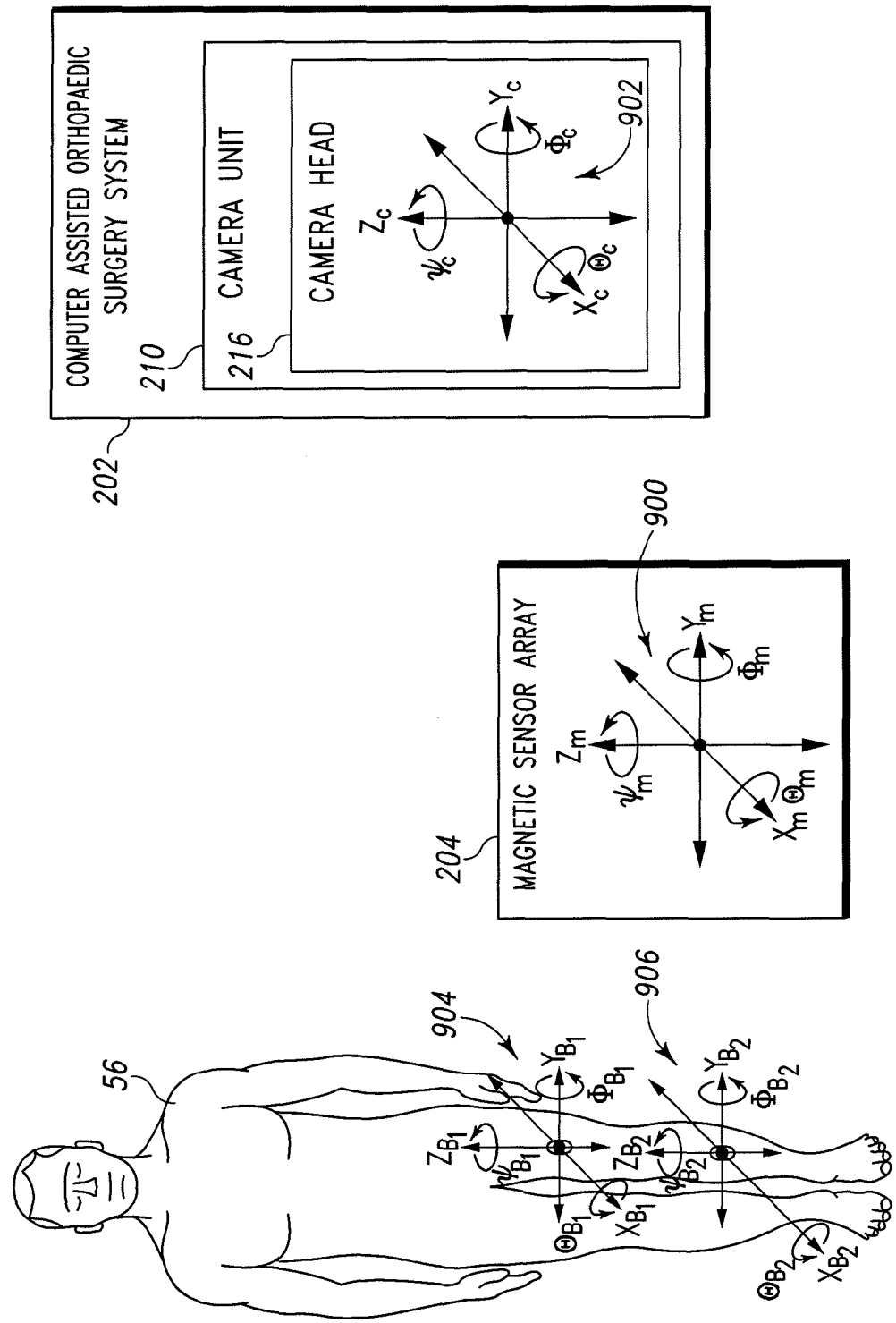
FIG. 19 is a block diagram of a number of coordinate systems of a computer assisted orthopaedic surgery system.

The positions of the magnets 400, the magnetic sensor array 204, and the bone or bony anatomy are determined with respect to respective coordinate systems. For example, as illustrated in FIG. 19, the magnetic sensor array 204 (e.g., the reference array 244 coupled to the magnetic sensor array 204) defines a magnetic sensor array coordinate system 900. The position of the magnets 400 are determined in process step 604 in reference to the magnetic sensor array coordinate system 900. Similarly, the camera head 216 of the camera unit 210 of the computer assisted orthopaedic surgery system 202 defines a global or computer assisted orthopaedic surgery system coordinate system 902. The position of the magnetic sensor array 204 is determined in process step 606 in reference to the global coordinate system 902. Similarly, the position of the relevant bone or bony anatomy (based on the position of the reference array(s) 218 coupled thereto) are determined in process step 608 in reference to the global coordinate system 902. In addition, each reference array coupled to the bones or bony anatomy of the patient 56 defines a bone coordinate system. For example, a reference array coupled to the femur of the patient 56 defines a first bone coordinate system 904 and a reference array coupled to the tibia of the patient 56 defines a second bone coordinate system 906 as illustrated in FIG. 19. As discussed in detail below, the position of the magnets 400 is determined first in the magnetic sensor array coordinate system 900 and subsequently transformed to the respective bone coordinate system 904, 906. That is, the position of a particular magnet 400 is transformed from the magnetic sensor array coordinate system 900 to the bone coordinate system 904, 906 of the particular bone in which the magnet is implanted or otherwise coupled to.

To determine the position of the magnet(s) 400 in the magnetic sensor array coordinate system 900 in process step

Figure 14:
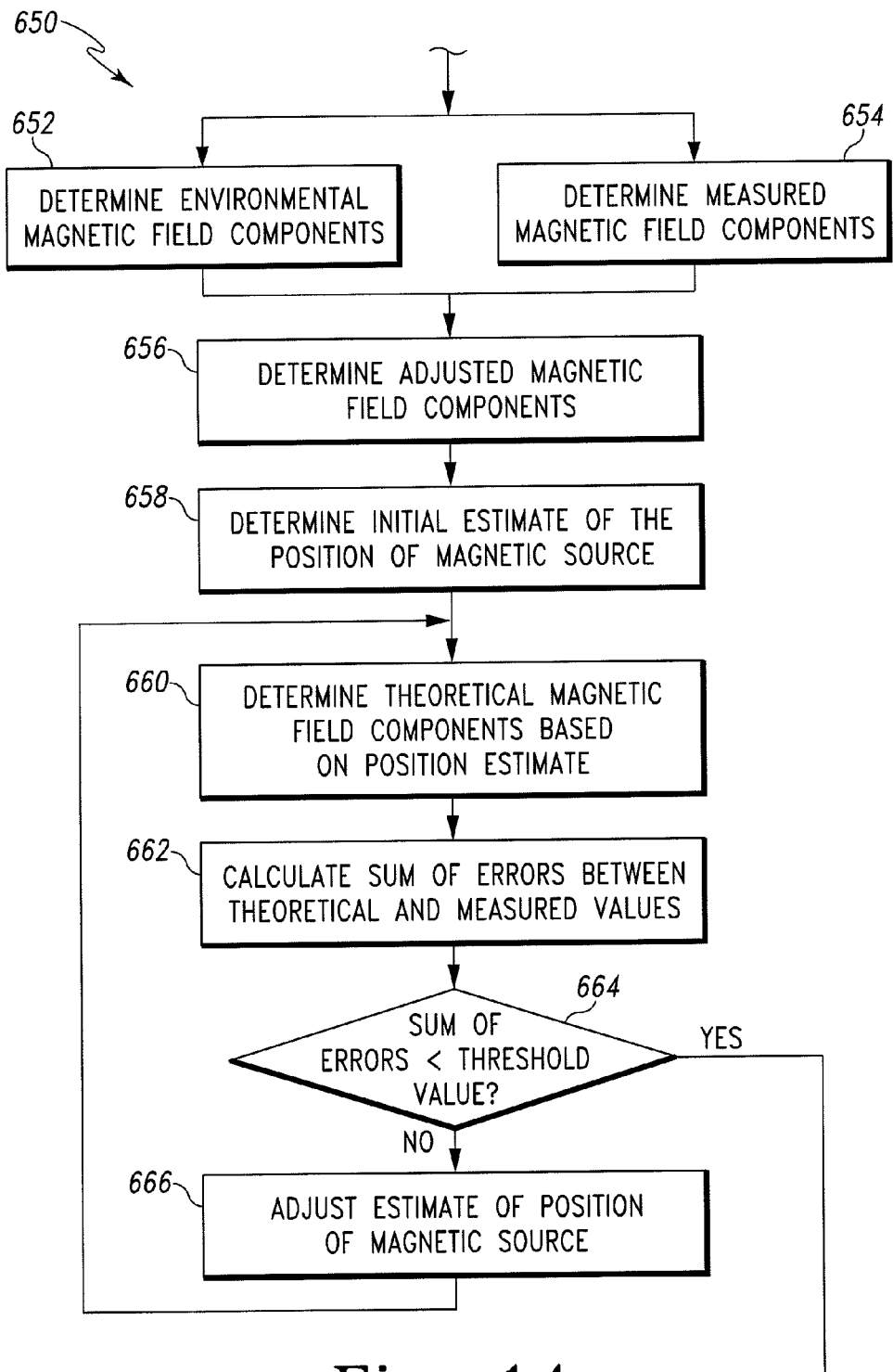
FIG. 14 is a simplified flowchart of an algorithm for determining a position of a magnetic source in a magnetic sensor array coordinate system.

604, the magnetic sensor array 204 may execute an algorithm 650 for determining a position of a magnet 400 as illustrated in FIG. 14. The algorithm 650 begins with process steps 652 and 654. As illustrated in FIG. 14, the process steps 652 and 654 may be executed contemporaneously with each other or in any order. In process step 652, undesirable environmental magnetic fields that may cause errors in the measurements of the magnetic sensors 350 are measured. The accuracy of the measurements of the magnetic sensors 350 may be improved by compensating the magnetic sensor array 204 for these undesirable, adverse factors. The environmental magnetic fields which are measured in process step 652 may include the Earth's magnetic field and magnetic fields generated from other equipment located in the surgical room, electrical cables, iron constructions, vehicles, and other stray or undesirable magnetic fields generated by sources other than the magnetic source 206 which may interfere with the magnetic fields generated by the magnetic source 206. For example, the Earth's magnetic field may adversely affect the measurements of the magnetic sensors 350 by interfering (i.e., constructively or destructively) with the magnetic field generated by the magnetic source 206. Because the Earth's magnetic field is continuously changing, a fixed adjustment value or offset for the magnetic sensors 350 is not available. However, as discussed above in regard to FIGS. 7, by using a remote magnetic sensor coupled to the magnetic sensor array 204, the effects of the Earth's magnetic field can be accounted for. That is, because the remote magnetic sensor is located apart from the sensor circuit 250 of the magnetic sensor array 204, the magnetic field generated by the magnetic source 206 has minimal impact on the measurements of the remote magnetic sensor. As such, the measurements of the remote magnetic sensor are generated primarily in response to the Earth's magnetic field and other environmental magnetic fields such as those caused by other surgical equipment located in the operating room and the like. Therefore, in process step 652, the measurements of the remote magnetic sensor are sampled.

In process step 654, the components of the three-dimensional magnetic flux density of the magnet 400 at various positions are measured. To do so, the output of each of the magnetic sensors 350 is sampled. As discussed above in regard to FIG. 9, some of the magnetic sensors 350 are three-dimensional magnetic sensors and, as such, measure the magnitude of each component at a given position of the magnetic flux density of the magnet 400. Other magnetic sensors 350 are one-dimensional magnetic sensors and are configured to measure the magnitude of only one component of the magnetic flux density. In the illustrative embodiment of FIG. 9, a total of twenty seven component measurements are generated by the magnetic sensors 350 (i.e., five three-dimensional magnetic sensors and twelve one-dimensional magnetic sensors). The magnetic field measurements may be stored in a suitable memory device for subsequent processing as described below. The sampling rate of the magnetic sensors 350 may be of rate useable or sustainable by the processing circuit 352

Contemporaneously with or during predetermined periods of the measurement process of the magnetic sensors 350 (e.g., during the positioning of the magnetic sensor array 204 in process step 602 of the algorithm 600), the sensor circuit 250 may be configured to perform a number of test procedures. To do so, the sensor circuit 250 may include one or more test circuits configured to perform one or more test algorithms. For example, the test circuits may be configured to measure the supply voltage of the sensor circuit 250 and produce an error if the supply voltage is below a predetermined minimum threshold or above a predetermined maximum threshold.

Additionally, the sensor circuit 250 may be configured to monitor the output of the magnetic sensors 350 and produce an error (e.g., activate an indicator to alert the user of the magnetic sensor array 204) if the voltage levels of the output signals of the sensors 350 are above a predetermined maximum threshold (i.e., the magnetic sensors 350 are in saturation) or below a predetermined minimum threshold (i.e., below the noise floor of the magnetic sensors 350). Additionally, in some embodiments, the sensor circuit 250 may include one or more compensation circuits to compensate or adjust the measurement values of the magnetic sensors 350 for such factors as temperature or the like.

Subsequently, in process step 656, the measurements of the magnetic sensors 350 are compensated or adjusted for the undesirable environmental magnetic fields. To do so, in one embodiment, the measurements of the magnetic sensors 350 are adjusted by subtracting the measurements of the remote magnetic sensor 386. In this way, the magnetic field errors caused by the Earth's magnetic field and other environmental magnetic fields are adjusted out of the measurement data produced by the magnetic sensors 350 and the overall accuracy of the magnetic sensor array 204 in measuring the magnetic flux density generated primarily from the magnetic source 206 is improved.

In process step 658, an initial estimate of the position of the magnet 400 is determined. The initial estimate includes an estimate of the values of the five degrees of freedom of the magnet 400. That is, the initial estimate includes an X-coordinate value, a Y-coordinate value, a Z-coordinate value, a (theta) $\theta$-rotational value about the X-axis, and a (phi) $\phi$-rotational value about the Y-axis of the magnet 400. In one particular embodiment, the X-, Y-, and Z-coordinate values are the coordinate values of the particular magnetic sensor 350 with respect to the centroid of the magnet 400. That is, the X-, Y-, and Z-coordinate values are estimates of the position of the magnetic sensor 350 in a three-dimensional coordinate system wherein the centroid of the magnet 400 is defined as the center of the coordinate system (i.e., the centroid of the magnet 400 lies at point (0, 0, 0)). Estimating the location of the magnet 400 in this manner allows calculations of the magnetic flux density using positive values for the X-, Y-, and Z-coordinate estimated values.

The estimated values may be any values and, in some embodiments, are predetermined seeded values that are used for measurement processes. However, by selecting an initial estimate closer to the actual position of the magnet 400, the speed and accuracy of the algorithm 650 may be improved. To do so, knowledge of the position of the magnetic sensor array 204 with respect to the magnet 400 may be used. That is, as discussed above in process step 602 of algorithm 600, the magnetic sensor array 204 is positioned such that the array 204 is on-axis or near on-axis with the magnetic moment of the magnet 400. As such, in one embodiment, the initial estimate of the location of the magnet 400 with respect to the magnetic sensor array 204 includes an estimated X-coordinate value of zero and an estimate Y-coordinate value of zero. Additionally, the (theta) $\theta$-rotational value and the a (phi) $\phi$-rotational value of the magnet 400 may be estimated as zero (e.g., it may be assumed that the sensor board 370 of the magnetic sensor array 204 is positioned orthogonal to the longitudinal axis of the magnet 400). The Z-coordinate value may also be estimated at zero. However, for additional accuracy, the Z-coordinate value may be estimated based on the average magnetic flux density of the Z-vector of the magnetic flux density of the magnet 400 as measured by the magnetic sensors 350 (i.e., those magnetic sensors 350 configured to measure the Z-vector of the three-dimensional magnetic field of the magnet 400). However, other estimated values may be used in other embodiments.

Once the initial estimated position of the magnet 400 is determined in process step 658, the components of the theoretical three-dimensional magnetic flux density of the magnet 400 at various points in space are calculated in process step 660. During the first iteration of the algorithm 650, the five degrees of freedom values of the magnet 400 estimated in process step 658 are used to determine each component of the theoretical three-dimensional magnetic flux density. However, as discussed below in regard to process step 666, in subsequent iterations of the algorithm 650, revised estimated values of the five degrees of freedom of the magnet 400 are used in process step 660.

The theoretical three-dimensional magnetic flux density of the magnet 400 at each sensor's 350 position at a point in space about the magnet 400 may be calculated using any suitable equation(s) and/or algorithms. In one particular embodiment, the following equations are used to calculate the magnitude of the magnetic flux density components (i.e., the X-, Y-, and Z-components) of the magnet 400.

$$B_x = \frac{\mu m \left[ \frac{3x(x\sin(\Theta)\cos(\Phi) + y\sin(\Theta)\sin(\Phi) + z\cos(\Theta))}{r^2} - \sin(\Theta)\cos(\Phi) \right]}{4\pi r^3}$$

$$B_y = \frac{\mu m \left[ \frac{3y(x\sin(\Theta)\cos(\Phi) + y\sin(\Theta)\sin(\Phi) + z\cos(\Theta))}{r^2} - \sin(\Theta)\sin(\Phi) \right]}{4\pi r^3}$$

$$B_z = \frac{\mu m \left[ \frac{3z(x\sin(\Theta)\cos(\Phi) + y\sin(\Theta)\sin(\Phi) + z\cos(\Theta))}{r^2} - \cos(\Phi) \right]}{4\pi r^3}$$

wherein $\mu$ is the permeability of free space (i.e., about $4*\pi*10^{-17}$ WbA$^{-1}$m$^{-1}$), m is the magnitude of the magnetic moment of the magnet 400 in units of Am$^2$, and $r=\sqrt{x^2+y^2+z^2}$ (in distance units).

Once the theoretical magnetic flux densities are calculated in process step 660, the sum of the error between the theoretical magnetic flux density component values and the measured magnetic flux density values as determined in process step 654 is calculated in process step 662. That is, the difference between the theoretical magnetic flux density component values and the measured magnetic flux density component values for each magnetic sensor 350 is calculated. The calculated differences for each magnetic sensor 350 is then summed. To do so, in one particular embodiment, the following objective function may be used.

$$F = \sum_{i=0}^{n} w_i (B_{th_i} - B_{me_i})^2$$

wherein n is the number of magnetic flux density components measured, $B_{th}$ is the theoretical magnitude of the ith magnetic flux density component of the magnet 400 at a given sensor position, $B_{me}$ is the measured magnitude of the ith magnetic flux density component of the magnet 400 at a given position, and $w_i$ is a weighting factor for the ith magnetic flux density component. The weighting factor, $w_i$, may be used to emphasize or minimize the effect of certain magnetic sensors 350. For example, in some embodiments, the magnetic sensors 350 positioned toward the center of the sensor board 370 may be given a higher weighting factor than the magnetic sensors 350 positioned toward the perimeter of the sensor board 370. In one particular embodiment, the weighting factors, $w_i$, are normalized weighting factors (i.e., range from a value of 0 to a value of 1). Additionally, other weighting schemes may be used. For example, each weighting factors, $w_i$, may be based on the magnetic field sensitivity of the particular magnetic sensor 350 measuring the ith magnetic flux density component. Alternatively, the weighting factors, $w_i$, may be based on the standard deviation divided by the mean of a predetermined number of samples for each magnetic sensor 350. In other embodiments, the weighting factors, $w_i$, may be used to selectively ignore sensors that are saturated or under the noise floor of the magnetic sensor 350. Still further, a combination of these weighting schemes may be used in some embodiments.

In process step 664, the algorithm 650 determines if the value of the objective function determined in process step 662 is below a predetermined threshold value. The predetermined threshold value is selected such that once the objective function falls below the threshold value, the position of the magnetic source 206 (i.e., the magnet 400) with respect to the magnetic sensor array 206 is known within an acceptable tolerance level. In one particular embodiment, the predetermined threshold value is 0.0. However, to increase the speed of convergence of the algorithm 650 on or below the predetermined threshold value, threshold values greater than 0.0 may be used in other embodiments.

If the objective function (i.e., the sum of errors) is determined to be below the predetermined threshold value, the algorithm 650 completes execution. However, if the objective function is determined to be greater than the predetermined threshold value in process step 664, the algorithm advances to process step 666. In process step 666, the estimate of the position of the magnetic source is adjusted. That is, in the first iteration of the algorithm 650, the initial estimate for the X-coordinate value, the Y-coordinate value, the Z-coordinate value, the (theta) $\theta$-rotational value about the X axis, and the (phi) $\phi$-rotational value about the Y axis of the magnet 400 are adjusted. A local optimization algorithm or a global optimization algorithm may be used. Any suitable local or global optimization algorithm may be used. Selection of the local or global optimization algorithm may be based on, for example, the speed of convergence of the algorithm, the accuracy of the solution, and/or the ease of implementation from a software and/or hardware standpoint.

Once a new estimate for the position of the magnet 400 (in five degrees of freedom) has been determined, the algorithm 650 loops back to process step 660 in which the theoretical magnetic flux density component values are determined using the new estimates calculated in process step 666. In this way, the algorithm 650 performs an iterative loop using the local/global optimization algorithm until the objective function converges to or below the predetermined threshold value. As discussed above, once the objective function has so converged, the five degrees of freedom of the magnet 400 is known.

It should be appreciated that in some embodiments the algorithm 650 is executed solely by the magnetic sensor array 204. However, in other embodiments, the magnetic sensor array 204 may be configured only to measure the magnetic flux density components of the magnet 400 in process step 654. In such embodiments, the process steps 656-666 are executed by the controller 208. To do so, the sensor circuit 250 of the magnetic sensor array 204 is configured to transmit the magnetic field measurement values of each magnetic sensor 350 to the controller 202

Referring back to algorithm 600 illustrated in FIG. 13, once the position of each magnet 400 relative to the magnetic sensor array 204 is determined in process step 604, such positions are converted to a point-and-direction format. That is, in some embodiments, the magnetic sensor array 204 may be configured to define the position of the magnets 400 using coordinate and rotational values (e.g., an X-coordinate value, a Y-coordinate value, a Z-coordinate value, a (theta) θ-rotational value about the X axis, and a (phi) φ-rotational value about the Y axis). If so, such position is converted to a point-and-direction format in process step 610 by determining the location of the centroid 404, $P_M$, and direction of the polar axis 406, $D_M$, of each magnet 400 in the magnetic sensor array coordinate system 900 based on the position data. As disclosed above, the direction of the polar axis 406 may be defined using unit vectors. The position of the magnets 400 may be so converted by the sensor circuit 250 of the magnetic sensor array 204 before transmitting the position data to the controller 204 or by the controller 204 after the magnetic sensor array 204 has transmitted the position data. Regardless, once the position of the magnets 400 in the magnetic sensor array coordinate system 900 has been determined, the algorithm 600 advances to process step 612.

Referring back to process step 606, contemporaneously with the determination of the position of the current magnet 400 in process steps 604 and 610, the controller 202 determines the position of the magnetic sensor array 204 and the relevant bony anatomy in process steps 606, 608. To do so, in process step 606, the controller 202 determines a transformation matrix for transforming the magnetic sensor array coordinate system 900 to the global coordinate system 902. Similarly, in process step 608, the controller determines a transformation matrix for transforming the bone coordinate systems 904, 906 to the global coordinate system 902. Each transformation matrix so determined is similar and includes a rotational component and a translational component. For example, the controller 202 may determine a transformation matrix, RT, as follows:

$$RT = \begin{bmatrix} \cos(\Psi)\cos(\Phi) + \sin(\Psi)\sin(\Phi)\sin(\Theta) & \sin(\Psi)\cos(\Phi) - \cos(\Psi)\sin(\Phi)\sin(\Theta) & \cos(\Theta)\sin(\Phi) & T_x \\ -\sin(\Psi)\cos(\Theta) & \cos(\Psi)\cos(\Theta) & \sin(\Theta) & T_y \\ \sin(\Psi)\sin(\Theta)\cos(\Phi) - \cos(\Psi)\sin(\Phi) & -\cos(\Psi)\sin(\Theta)\cos(\Phi) - \sin(\Psi)\sin(\Phi) & \cos(\Theta)\cos(\Phi) & T_{xz} \\ 0 & 0 & 0 & 1 \end{bmatrix}$$

wherein $T_x$ is the translation coordinate value in the X-axis, $T_y$ is the translation coordinate value in the Y-axis, $T_z$ is the translation coordinate value in the Z-axis, Θ (theta) is the rotational value about the X-axis, Φ (phi) is the rotational value about the Y-axis, and Ψ (psi) is the rotational value about the Z-axis. The transformation matrices are used by the controller 202 to determine the proper position in which to display indicia on the display device 212. That is, the position of an item of interest can be determined in the global coordinate system 902 by multiplying the position of the item of interest in the magnetic sensor array coordinate system 900 or one of the bone coordinate systems 904, 906 by the appropriate transformation matrix.

Once the magnetic sensor array 204 (and/or controller 302) has determined the position of the current magnet 400 in the magnetic sensor array coordinate system 900 and the controller 302 has determined the position of the magnetic sensor array 204 and relevant bony anatomy in the global coordinate system 902, the position of the current magnet is transformed from the magnetic sensor array coordinate system 900 to the respective bone coordinate system 904, 906 in process step 612. To do so, the location of the centroid 404 and the direction of the polar axis 406 of the current magnet 400 is transformed to the respective bone coordinate system 904, 906. The location of the centroid 404 may be transformed using the following equation:

$$P_B = RT[2]^{-1} * (RT[1] * P_M)$$

wherein $P_B$ is the location vector (i.e., X-coordinate value, Y-coordinate value, and Z-coordinate value) of the centroid 404 of the current magnet 400 in the respective bone coordinate system 904, 906, RT[2] is the transformation matrix determined by the controller 202 to transform the bone coordinate system 904, 906 to the global coordinate system 902 ($RT[2]^{-1}$ is the inverse of such matrix), RT[1] is the transformation matrix determined by the controller 202 to transform the magnetic sensor array coordinate system 900 to the global coordinate system 902, and $P_M$ is the location vector of the centroid of the magnet 400 in the magnetic sensor array coordinate system 900. Because $P_M$ is a 3×1 matrix and RT[1] is a 4×4 matrix, a value of 1 may be added to the column of $P_M$ to form a 4×1 matrix. Such a calculation will result in a 4×1 $P_B$ matrix, wherein the last column value, which is equal to 1, is ignored.

The direction of the polar axis 406 of the current magnet 400 in the respective bone coordinate system 904, 906 is also determined in process step 612. Because the direction of the polar axis 406 is defined in a unit vector format, the direction vector does not need to be translated from the magnetic sensor array coordinate system 900. That is, the direction of the polar axis 406 of the current magnet may be determined in the respective bone coordinate system 904, 906 by multiplying the direction vector of the polar axis 406 in the magnetic sensor array coordinate system 900 by a rotational matrix determined by the controller 208. The rotational matrix is equal to the upper-left 3×3 matrix of the RT transformation matrix described above and may be determined as follows:

$$R = \begin{bmatrix} \cos(\Psi)\cos(\Phi) + \sin(\Psi)\sin(\Phi)\sin(\Theta) & \sin(\Psi)\cos(\Phi) - \cos(\Psi)\sin(\Phi)\sin(\Theta) & \cos(\Theta)\sin(\Phi) \\ -\sin(\Psi)\cos(\Theta) & \cos(\Psi)\cos(\Theta) & \sin(\Theta) \\ \sin(\Psi)\sin(\Theta)\cos(\Phi) - \cos(\Psi)\sin(\Phi) & -\cos(\Psi)\sin(\Theta)\cos(\Phi) - \sin(\Psi)\sin(\Phi) & \cos(\Theta)\cos(\Phi) \end{bmatrix}$$

wherein Θ (theta) is the rotational value about the X-axis, Φ (phi) is the rotational value about the Y-axis, and Ψ (psi) is the rotational value about the Z-axis. As such, the direction of polar axis 406 may be transformed from the magnetic sensor array coordinate system 900 to the respective bone coordinate system 904, 906 using the following equation:

$$D_B = R[2]^{-1} * (R[1] * D_M)$$

wherein $D_B$ is the direction unit vector (i.e., X-coordinate value, Y-coordinate value, and Z-coordinate value) of the centroid 404 of the current magnet 400 in the respective bone coordinate system 904, 906, R[2] is the rotational matrix of the transformation matrix RT[2] determined by the controller 202 to transform the bone coordinate system 904, 906 to the global coordinate system 902 ($R[2]^{-1}$ is the inverse of such matrix), R[1] is the rotational matrix of the transformation matrix RT[1] determined by the controller 202 to transform the magnetic sensor array coordinate system 900 to the global coordinate system 902, and $P_M$ is the location vector of the centroid of the magnet 400 in the magnetic sensor array coordinate system 900.

Once the position of the current magnet 400 in the respective bone coordinate system 904, 906 has been determined in process step 612, the controller 208 determines if the current magnet 400 is the last magnet 400 of the magnetic source 206. The controller 208 may be instructed that the current magnet is the last magnet 400 by, for example, entering appropriate information into the controller 208. If the current magnet 400 is not the last magnet of the magnetic source 206, the algorithm 600 loops back to process step 602 wherein the magnetic sensor array 204 is positioned near the next magnet 400 of the magnetic source 206. Again, as discussed above, the magnetic sensor array 204 is positioned near the magnets 400 in a predetermined order such that the position data of each magnet 400 is associated with the correct magnet 400 of the three-dimensional image 850, 860 by the controller 208.

Figure 15:
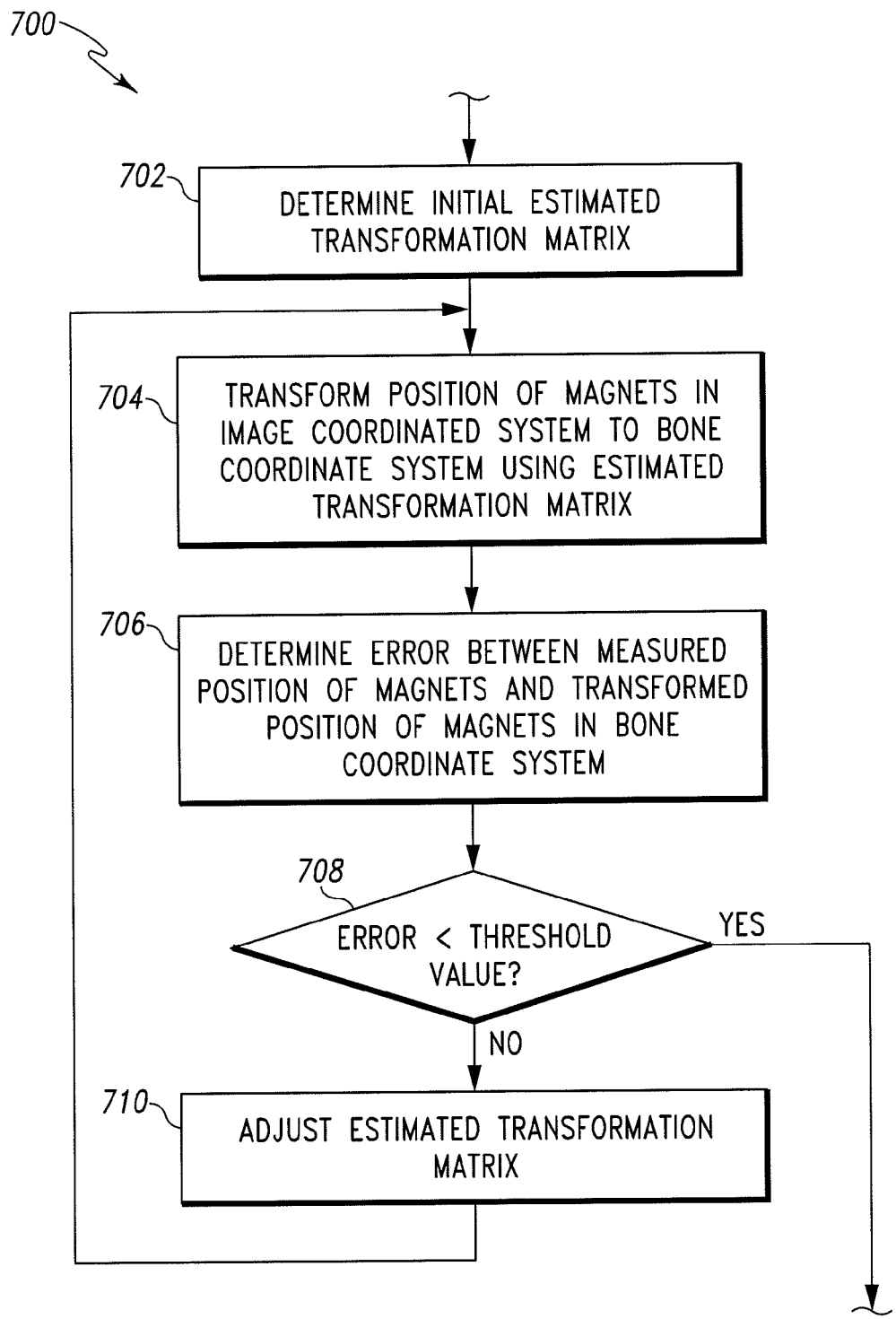
FIG. 15 is a simplified flowchart for determining a transformation matrix for transforming an image coordinate system to a bone coordinate system.

If, however, the current magnet 400 is the last magnet 400 of the magnetic source 206, the algorithm 600 advances to process step 616. In process step 616, the controller 206 is configured to determine a transformation matrix for transforming the image coordinate system 856 of the three-dimensional image 850, 860 (see FIGS. 18 and 19) to each of the bone coordinate systems 904, 906. To do so, the controller 206 may execute an algorithm 700 for determining such a transformation matrix as illustrated in FIG. 15. The algorithm 700 begins with process step 702 in which an initial estimate of the transformation matrix, $RT_I$, is determined. That is, a matrix for transforming the image coordinate system 856 to each bone coordinate system 904, 906 is determined. The transformation matrix may be populated with any estimated values and, in some embodiments, are predetermined seeded values. However, by selecting an initial estimated transformation matrix closer to the accurate transformation matrix, the speed and accuracy of the algorithm 700 may be improved. To do so, in some embodiments, the controller 208 may be configured to determine a transformation matrix required to align the centroid 404 and the long axis 406 of one of the magnets 400 in the image coordinate system 846 to the centroid 404 and the long axis 406 of respective magnetic source 400 in the bone coordinate systems 904, 906. Because such a transformation matrix correlates only a single magnet 400 between the image coordinate system 846 and the bone coordinate system 904, 906, the calculation of the transform matrix is simplified and, thereby, a relatively fast computation. The remaining magnets 400 may or may not be aligned between the image coordinate system 846 and the bone coordinate system 904, 906. Regardless, such an initial estimated transformation matrix provides an initial matrix, which the controller 208 refines to improve the correlation between the image coordinate system 846 and the bone coordinate system 904, 906 as discussed in detail below.

Additionally or alternatively, previously determined matrices may be used as the initial estimate in some embodiments. For example, when the controller 208 determines a transformation matrix, $RT_I$, during an orthopaedic surgical procedure, such a matrix may be stored in the memory device 224, the database 226, or the remote database 228. Subsequently, during the next surgical procedure, the controller 208 may be configured to retrieve the stored transformation matrix and use such matrix as the initial estimate. In such embodiments, an assumption is made that the patient 56 is substantially similarly located with respect to the computer assisted orthopaedic surgery system 202.

Regardless, once an initial transformation matrix, $RT_I$, is estimated in process step 702, the positions of the magnets 400 in the image coordinate system 856 are transformed to the respective bone coordinate system 904, 906 using the estimated transformation matrix. As discussed above in regard to process step 558 of algorithm 550 illustrated in FIG. 12, the position of the magnets 400 in the three-dimensional image 850, 860 is represented as a point (a three-dimensional vector including an X-coordinate value, a Y-coordinate value, and a Z-coordinate value of the position of the centroid 404) and a direction (a three-dimensional unit vector of the direction of the polar axis 406). As such, the location of the centroid 404 of each magnet 400 may be transformed from the image coordinate system 856 to the respective bone coordinate system by the following equation:

$$P_B' = RT_I * P_I$$

wherein $P_B'$ is the calculated location vector (i.e., X-coordinate value, Y-coordinate value, and Z-coordinate value) of the centroid 404 of the magnet 400 in the respective bone coordinate system 904, 906, $RT_I$ is the estimated transformation matrix to transform the image coordinate system 856 to the respective bone coordinate system 904, 906, and $P_I$ is the location vector of the centroid of the magnet 400 in the image coordinate system 856. Again, because $P_I$ is a 3×1 matrix and $RT_I$ is a 4×4 matrix, a value of 1 may be appended to the last row of $P_I$ to form a 4×1 matrix.

The direction of the polar axis 406 of the current magnet 400 in the respective bone coordinate system 904, 906 is also determined. Again, because the direction of the polar axis 406 is defined in a unit vector format, the direction vector does not need to be translated from the image coordinate system 856. As such, the location of the direction of the polar axis 406 of each magnet 400 may be transformed from the image coordinate system 856 to the respective bone coordinate system 904, 906 using the estimated rotation matrix (the upper-left 3×3 matrix of the estimated transformation matrix $RT_I$) by the following equation:

$$D_B' = R_I * D_I$$

wherein $D_B'$ is the calculated direction unit vector (i.e., X-coordinate value, Y-coordinate value, and Z-coordinate value) of the polar axis 406 of the current magnet 400 in the respective bone coordinate system 904, 906, $R_I$ is the rotational matrix of the estimated transformation matrix to transform the image coordinate system 856 to the respective bone coordinate system 904, 906, and $D_I$ is the direction vector of the polar axis 406 of the magnet 400 in the image coordinate system 856.

Once the transformed position of the magnets 400 have been determined in process step 706, the sum of the error between the transformed position of the magnets 400 as determined in process step 706 and the measured position of the magnets 400 in the bone coordinate system 904, 906 as determined in process step 612 of algorithm 600 is calculated in process step 708. That is, the difference between the transformed position and the measured position for each magnet 400 is calculated. The calculated differences for each magnet 400 is then summed. To do so, in one particular embodiment, the following objective function may be used.

$$F = \min\left(\sum_{i=1}^{n}(P_{B_i} - P_{I_i})^2 + \sum_{i=1}^{n}(D_{B_i} - D_{B_i})^2\right)$$

wherein n is the number of magnets 400, $P_B$ is the measured position vector of the centroid 404 of the magnet i transformed from the magnetic sensor array coordinate system 900, $P_I$ is the position vector of the centroid 404 of the magnet i transformed from the image coordinate system 856 using the estimated transformation matrix, $D_B$ is the measured direction vector of the polar axis 406 of the magnet i transformed from the magnetic sensor array coordinate system 900, and $D_I$ is the position vector of the polar axis 406 of the magnet i transformed from the image coordinate system 856 using the estimated transformation matrix. In other embodiments, other types of objectives functions may be used to determine the sum of the error between the transformed and measured position of the magnets 400. For example, in some embodiments, the square root of the sum of the squares of errors may be determined. Additionally, in some embodiments, the objective function may also include one or more weighting factors applied to those terms having a higher degree of measurement confidence. For example, a weighting factor may be applied to the position terms of a particular magnet 400.

In process step 708, the algorithm 700 determines if the value of the objective function determined in process step 706 is below a predetermined threshold value. The predetermined threshold value is selected such that once the objective function falls below the threshold value, the estimated transformation matrix, $RT_I$, transforms the image coordinate system to the respective bone coordinate systems 904, 906 within an acceptable tolerance level. In one particular embodiment, the predetermined threshold value is 0.0. However, to increase the speed of convergence of the algorithm 700 on or below the predetermined threshold value, threshold values greater than 0.0 may be used in other embodiments.

If the objective function (i.e., the sum of errors) is determined to be below the predetermined threshold value, the algorithm 700 completes execution. However, if the objective function is determined to be greater than the predetermined threshold value in process step 708, the algorithm 700 advances to process step 710. In process step 710, the estimate of the transformation matrix, $RT_I$, is adjusted. A local optimization algorithm or a global optimization algorithm may be used to determine such an adjustment. Any suitable local or global optimization algorithm may be used. Selection of the local or global optimization algorithm may be based on, for example, the speed of convergence of the algorithm, the accuracy of the solution, and/or the ease of implementation from a software and/or hardware standpoint.

Once a new estimate for the transformation matrix, $RT_I$, has been determined, the algorithm 700 loops back to process step 704 in which the position of the magnets 400 is again transformed from the image coordinate system 856 to the respective bone coordinate system 904, 906 using the new estimated transformation matrix, $RT_I$. In this way, the algorithm 700 performs an iterative loop using the local/global optimization algorithm until the objective function converges to or below the predetermined threshold value. As discussed above, once the objective function has so converged, the transformation matrix, $RT_I$, is known.

Referring back to algorithm 500 in FIG. 11, after the bony anatomy has been registered in process step 516, the magnetic source 206 may be decoupled from the bone(s) of the patient in process step 518. To do so, the magnetic sensor array 204 may be used to determine the location of the magnets 400 that form the magnetic source 206. For example, the magnetic sensor array 204 may be passed over the skin of the patient until the indicator 360 of the magnetic sensor array 204 is activated, which indicates the magnetic sensor array 204 is in the magnetic field of at least one of the magnets 400. The magnets 400 may then be removed using an appropriate surgical procedure. In this way, the magnetic fields of the magnets 400 are prevented from interfering with the performance of the orthopaedic surgical procedure. For example, in embodiments wherein the reference arrays are embodied as wireless transmitters (i.e., electromagnetic sensor arrays) rather than reflective reference arrays, the magnetic source 206 may be decoupled from the bone(s) of the patient prior to the performance of the orthopaedic surgical procedure so as to avoid any magnetic interference with the operation of the reference arrays 54. Alternatively, if the magnetic source 206 is left coupled to the bone(s) of the patient during the performance of the orthopaedic surgical procedure, the bone(s) may be reregistered at any time and as often as necessary during the procedure.

Subsequently, in process step 520, the orthopaedic surgical procedure may be performed. During performance of the orthopaedic surgical procedure, the computer assisted orthopaedic surgery system 200 provides an amount of surgical navigation to the surgeon 50 by displaying the three-dimensional image(s) 850 of the relevant bony anatomy. Because the three-dimensional image(s) 850 is registered with the bone coordinate system 904, 906 via use of the transformation matrix determined in process step 616 of algorithm 600, the image(s) 850 are displayed to the surgeon on the display device 220 in a location and orientation based on the position of the reference arrays 218 coupled to the relevant bony anatomy. As such, the surgeon may use the system 200 to navigate and step through the orthopaedic surgical process in a similar manner as the CAOS system 10 illustrated in and described above in regard to FIGS. 1-6. It should be appreciated, however, that the present algorithm 500 for registering the bone anatomy of a patient may completely or partially replace the process step 106 of the algorithm 100 illustrated in and described above in regard to FIG. 6.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the system, and method described herein. It will be noted that alternative embodiments of the system and method of the present disclosure may not include all of the features described yet still benefit from at least some of the advantages of such features. Those of ordinary skill in the art may readily devise their own implementations of the system and method that incorporate one or more of the features of the present invention and fall within the spirit and scope of the present disclosure as defined by the appended claims.

The invention claimed is:

1. A method for registering a bone of a patient with a computer assisted orthopaedic surgery system, the method comprising:

retrieving an image of the bone including indicia of the position of a magnet implanted in the bone, the image defining an image coordinate system;

determining a position of a reference array coupled to the bone, the reference array defining a bone coordinate system;

determining first data indicative of the position of the magnet in the bone coordinate system by determining a location of the centroid of the magnet using the following equation:

$$P_B = RT[2]^{-1} * (RT[1] * P_M)$$

wherein $P_B$ the location of the centroid of the magnet in the bone coordinate system, RT[1] is a first transformation matrix, RT[2] is a second transformation matrix, and $P_M$ is the location of the centroid of the magnet in the magnetic sensor array coordinate system;

determining second data indicative of a correlation between the image coordinate system and the bone coordinate system based on the first data; and displaying an image of the bone in a position determined based on the second data.

2. The method of claim 1, wherein retrieving an image of the bone comprises retrieving a three-dimensional medical image of the bone of the patient.

3. The method of claim 1, wherein coupling a reference array to the bone of the patient comprises coupling a reference array to the bone of the patient selected from the group consisting of a reflective reference array and a radio frequency reference array.

4. The method of claim 1, wherein determining the first data comprises positioning a magnetic sensor array in a magnetic field generated by the magnet, the magnetic sensor array defining a magnetic sensor array coordinate system.

5. The method of claim 4, wherein determining the first data comprises measuring a magnetic flux density of the magnetic field at a plurality of points in space with a number of magnetic sensors of the magnetic sensor array.

6. The method of claim 4, wherein determining the first data comprises determining the position of the magnet in the magnetic sensor array coordinate system.

7. The method of claim 6, wherein determining the position of the magnetic source in the magnetic sensor array coordinate system comprises:

(i) determining the location of the centroid of the magnet coupled to the bone in the magnetic sensor array coordinate system, and (ii) determining the direction of a polar axis of the magnet in the magnetic sensor array coordinate system.

8. The method of claim 7, wherein determining the first data comprises:

(i) determining the position of the magnetic sensor array in a global coordinate system defined by a tracking unit of the computer assisted orthopaedic surgery system, and (ii) determining the position of the bone of the patient in the global coordinate system based on the position of the reference array.

9. The method of claim 1, wherein determining the first data further comprises determine a direction of the polar axis of the magnetic is determined using the following equation:

$$D_B = R[2]^{-1} * (R[1] * D_M)$$

wherein $D_B$ the direction of the polar axis of the magnet in the bone coordinate system, R[2] is the second transformation matrix, and R[1] is the first transformation matrix, and $D_M$ is the direction of the polar axis of the magnet in the magnetic sensor array coordinate system.

10. The method of claim 1, wherein determining second data indicative of a correlation between the image coordinate system and the bone coordinate system comprises determining a transformation matrix.

11. The method of claim 10, wherein determining the transformation matrix comprises:

(i) estimating a transformation matrix for transforming the image coordinate system to the bone coordinate system, (ii) transforming the position of the magnet from the image coordinate system to the bone coordinate system using the estimated transformation matrix, (iii) generating third data indicative of the transformed position of the magnet, (iv) calculating a difference between the first data and the third data, and (v) repeating steps (i)-(iv) until the difference between the first data and the third data is less than a predetermined minimum threshold value.

12. The method of claim 11, wherein calculating a difference between the first data and the third data comprises calculating a sum of the squared difference between the first data and the third data.

13. The method of claim 11, wherein displaying the image of the bone comprises displaying an image of the bone in a location and orientation determined using the estimated transformation matrix.

14. The method of claim 11, wherein the magnet comprises a magnet and the first and second data comprise location data indicative of the location of the centroid of the magnet and direction data indicative of the direction of a polar axis of the magnet.

15. A system for registering a bone of a patient to with a computer assisted orthopaedic surgery system, the system comprising:

a first reference array configured to be coupled to the bone of the patient, the first reference array defining a first coordinate system;

a display device;

a processor electrically coupled to the display device; and a memory device electrically coupled to the processor, the memory device having stored therein a plurality of instructions, which when executed by the processor, cause the processor to:

retrieve an image of the bone including indicia of the position of a magnet coupled to the bone, the image defining a second coordinate system;

determine first data indicative of the position of the magnet in the first coordinate system by determining a location of the centroid of the magnet using the following equation:

$$P_B = RT[2]^{-1} * (RT[1] * P_M)$$

wherein $P_B$ the location of the centroid of the magnet in the bone coordinate system, RT[1] is a first transformation matrix, RT[2] is a second transformation matrix, and $P_M$ is the location of the centroid of the magnet in the magnetic sensor array coordinate system;

determine second data indicative of a correlation between the second coordinate system and the first coordinate system based on the first data; and display an image of the bone on the display device in a position determined based on the second data.

16. The system of claim 15, further comprising a magnetic sensor array having a second reference array coupled thereto, the second reference array defining a third coordinate system, wherein:
to determine first data comprises to determine the position of the magnet in the third coordinate system based on data received from the magnetic sensor array.

17. The system of claim 15, wherein to determine second data indicative of a correlation between the image coordinate system and the bone coordinate system comprises to determine a transformation matrix.

18. The system of claim 17, wherein to determine a transformation matrix comprises to:
(i) estimate a transformation matrix for transforming the image coordinate system to the bone coordinate system,
(ii) transform the position of the magnet from the image coordinate system to the bone coordinate system using the estimated transformation matrix,
(iii) generate third data indicative of the transformed position of the magnet,
(iv) calculate a difference between the first data and the third data, and
(v) repeat steps (i)-(iv) until the difference between the first data and the third data is less than a predetermined minimum threshold value.

19. A method for registering a bone of a patient with a computer assisted orthopaedic surgery system, the method comprising:
determining the position of a magnet implanted in the bone in a first coordinate system defined by a magnetic sensor array;
transforming the position of the magnet from the first coordinate system to a second coordinate system defined by a reference array coupled to the bone by determining the location of a centroid of the magnet using the following equation:

$$P_B = RT[2]^{-1} * (RT[1] * P_M)$$

wherein $P_B$ the location of the centroid of the magnet in the bone coordinate system, RT[1] is a first transformation matrix, RT[2] is a second transformation matrix, and $P_M$ is the location of the centroid of the magnet in the magnetic sensor array coordinate system;
generating first data indicative of the position of the magnet in the second coordinate system;
retrieving an image of the bone having indicia of the position of the magnet, the image defining a third coordinate system;
determining a transformation matrix for transforming the position of the magnet from the third coordinate system to the second coordinate system based on the first data; and
displaying an image of the bone in a location and orientation determined using the transformation matrix.

20. The method of claim 19, wherein determining the position of a magnet coupled to the bone in the first coordinate system comprises:
(i) determining the location of the centroid of the magnet in the first coordinate system, and
(ii) determining the direction of a polar axis of the magnet in the first coordinate system.

21. The method of claim 19, wherein generating first data indicative of the position of the magnet in the second coordinate system comprises:
(i) determining the location of the centroid of the magnet in the second coordinate system, and
(ii) determining the direction of a polar axis of the magnet in the second coordinate system.

22. The method of claim 19, wherein determining a transformation matrix for transforming the position of the magnet from the third coordinate system to the second coordinate system comprises
(i) determining an estimated transformation matrix for transforming the third coordinate system to the second coordinate system,
(ii) transforming the position of the magnet from the third coordinate system to the second coordinate system using the estimated transformation matrix,
(iii) generating second data indicative of the transformed position of the magnet,
(iv) calculating a difference between the first data and the second data, and
(v) repeating steps (i)-(iv) until the difference between the first data and the second data is less than a predetermined minimum threshold value.

23. The method of claim 22, wherein calculating the difference between the first data and the second data comprises calculating a sum of the squared difference between the first data and the second data.

* * * * *